(12) United States Patent
Nabeshima et al.

(10) Patent No.: US 12,312,380 B2
(45) Date of Patent: May 27, 2025

(54) METHOD FOR PRODUCING ACTIVE GcMAF

(71) Applicant: FOUNDATION FOR BIOMEDICAL RESEARCH AND INNOVATION AT KOBE, Hyogo (JP)

(72) Inventors: Yo-Ichi Nabeshima, Hyogo (JP); Yoko Nabeshima, Hyogo (JP); Chiaki Abe, Hyogo (JP)

(73) Assignee: FOUNDATION FOR BIOMEDICAL RESEARCH AND INNOVATION AT KOBE, Hyogo (JP)

( * ) Notice: Subject to any disclaimer, the term of this patent is extended or adjusted under 35 U.S.C. 154(b) by 1206 days.

(21) Appl. No.: 16/771,781

(22) PCT Filed: Dec. 14, 2018

(86) PCT No.: PCT/JP2018/046149
§ 371 (c)(1),
(2) Date: Oct. 30, 2020

(87) PCT Pub. No.: WO2019/117295
PCT Pub. Date: Jun. 20, 2019

(65) Prior Publication Data
US 2021/0198307 A1 Jul. 1, 2021

(30) Foreign Application Priority Data
Dec. 15, 2017 (JP) .................................. 2017-241109

(51) Int. Cl.
*C12P 21/00* (2006.01)
*C07K 1/22* (2006.01)
*C12P 21/02* (2006.01)

(52) U.S. Cl.
CPC ................ *C07K 1/22* (2013.01); *C12P 21/02* (2013.01)

(58) Field of Classification Search
CPC ..................................................... C12P 21/00
See application file for complete search history.

(56) References Cited

U.S. PATENT DOCUMENTS

| | | | |
|---|---|---|---|
| 5,177,001 A | 1/1993 | Yamamoto | |
| 6,410,269 B1 | 6/2002 | Yamamoto | |
| 2004/0224877 A1 | 11/2004 | Pirie-Shepherd et al. | |
| 2013/0295593 A1 | 11/2013 | Beckert et al. | |
| 2016/0120946 A1 | 5/2016 | Margalit et al. | |

FOREIGN PATENT DOCUMENTS

| | | | |
|---|---|---|---|
| JP | 6-503716 | 4/1994 | |
| JP | 11-511962 | 10/1999 | |
| JP | 2003-532682 | 11/2003 | |
| JP | 2016-520646 | 7/2016 | |
| WO | WO9640903 | * 12/1996 | ............. C12N 15/10 |

OTHER PUBLICATIONS

Wielders et al. (2015) "Automated Competitive Protein-Binding Assay for Total 25-OH Vitamin D, Multicenter Evaluation and Practical Performance" Journal of Clinical Laboratory Analysis, 29(6), 451-461. (Year: 2015).*
Kim et al. (2010) "Mammalian cell transfection: the present and the future" Analytical and bioanalytical chemistry, 397, 3173-3178. (Year: 2010).*
Usta et al. (2014) "Chemically defined serum-free and xeno-free media for multiple cell lineages" Annals of translational medicine, 2 (10), 9 pages. (Year: 2014).*
Negrete et al. (2008) "Production of adenoviral vectors in 293 cells: A case study of the adaptation of attached cells to grow in suspension" The Open Biotechnology Journal, 2(1), 29-35. (Year: 2008).*
Swamy et al. (1995) "Affinity Purification of Human Plasma Vitamin-D-Binding Protein" Protein expression and purification, 6(2), 185-188. (Year: 1995).*
Jain et al. (Mar. 23, 2017) "A high density CHO-S transient transfection system: Comparison of ExpiCHO and Expi293" Protein Expression and Purification, 134, 38-46. (Year: 2017).*
Nabeshima et al. "Simple method for large-scale production of macrophage activating factor GcMAF" Sci Rep. Nov. 5, 2020; 10(1): 19122, 11 pages. (Year: 2020).*
International Search Report issued Mar. 12, 2019 in International (PCT) Application No. PCT/JP2018/046149.
Office Action issued Feb. 28, 2020 in corresponding Japanese Application No. 2019-559230, with English translation.
Yamamoto et al., "A defect in the inflammation-primed macrophage-activation cascade in osteopetrotic rats", J Immunol., May 1994, vol. 152, No. 10, pp. 5100-5107.
Schneider et al., "Effects of vitamin D binding protein-macrophage activating factor (DBP-MAF) infusion on bone resorption in two osteopetrotic mutations.", Bone, Jun. 1995, vol. 16, pp. 657-662.
Yamamoto et al., "Vitamin D3 Binding Protein (Group-Specific Component) Is a Precursor for the Macrophage-Activating Signal Factor From Lysophosphatidylcholine-Treated Lymphocytes", Proc Natl Acad Sci USA, Oct. 1991, vol. 88, No. 19, pp. 8539-8543.
Yamamoto et al., "Deglycosylation of serum vitamin D3-binding protein leads to immunosuppression in cancer patients", Cancer Res., Jun. 1996, vol. 56, No. 12, pp. 2827-2831.
Yamamoto et al., "Structural definition of a potent macrophage activating factor derived from vitamin D3-binding protein with adjuvant activity for antibody production", Mol Immunol., Oct. 1996, vol. 33, No. 15, pp. 1157-1164.

(Continued)

*Primary Examiner* — Laura Schuberg
*Assistant Examiner* — James Joseph Graber
(74) *Attorney, Agent, or Firm* — Wenderoth, Lind & Ponack, L.L.P.

(57) ABSTRACT

The purpose of the present invention is to provide a method for producing active GcMAF more simply and at a high yield. The present invention is a method for producing active GcMAF comprising a step for culturing host cells which are transfected with a VDBP expression vector in serum-free medium. This culture is preferably a suspension culture. In addition, this method for producing active GcMAF is also characterized by not requiring an enzyme treatment step for deglycosylation.

5 Claims, 6 Drawing Sheets

Specification includes a Sequence Listing.

(56) References Cited

OTHER PUBLICATIONS

Benis et al., "The effects of vitamin D binding protein-macrophage activating factor and colony-stimulating factor-1 on hematopoietic cells in normal and osteopetrotic rats", Blood, Oct. 1996, vol. 88, No. 8, pp. 2898-2905.

Korbelik et al., "Macrophage-directed immunotherapy as adjuvant to photodynamic therapy of cancer", Br J Cancer, 1997, vol. 75, No. 2, pp. 202-207.

Mohamad et al., "Characterization of Human Gc Protein-Derived Macrophage Activation Factor (GcMAF) and Its Functional Role in Macrophage Tumoricidal Activity", Adv Exp Med Biol., 2003, vol. 510, No. 77-82.

Yamamoto et al., "Immunotherapy of BALB/c mice bearing Ehrlich ascites tumor with vitamin D-binding protein-derived macrophage activating factor", Cancer Res., Jun. 1997, vol. 57, No. 11, pp. 2187-2192.

Uto et al., "Degalactosylated/Desialylated Bovine Colostrum Induces Macrophage Phagocytic Activity Independently of Inflammatory Cytokine Production", Anticancer Res., Aug. 2015, vol. 35, No. 8, pp. 4487-4492.

Adebanjo et al., "A possible new role for vitamin D-binding protein in osteoclast control: inhibition of extracellular Ca2+ sensing at low physiological concentrations", Biochem Biophys Res Commun., Aug. 1998, vol. 249, No. 3, pp. 668-671.

Smith et al., "Effects of Gc-Macrophage Activating Factor in Human Neurons; Implications for Treatment of Chronic Fatigue Syndrome", American Journal of Immunology, 2013, vol. 9, No. 4, pp. 120-129.

Rehder et al., "Glycosylation status of vitamin D binding protein in cancer patients", Protein Sci., Oct. 2009, vol. 18, No. 10, pp. 2036-2042.

Odgren et al., "The toothless osteopetrotic rat has a normal vitamin D-binding protein-macrophage activating factor (DBP-MAF) cascade and chondrodysplasia resistant to treatments with colony stimulating factor-1 (CSF-1) and/or DBP-MAF", Bone, Aug. 1999, vol. 25, No. 2, pp. 175-181.

Swamy et al., "Baculovirus-expressed vitamin D-binding protein-macrophage activating factor (DBP-maf) activates osteoclasts and binding of 25-hydroxyvitamin D(3) does not influence this activity", J Cell Biochem., 2001, vol. 81, No. 3, pp. 535-546.

Mohamad et al., "Tumor cell alpha-N-acetylgalactosaminidase activity and its involvement in GcMAF-related macrophage activation", Comp Biochem Physiol A Mol Integr Physiol., May 2002, vol. 132, No. 1, pp. 1-8.

Kanda et al., "Effects of vitamin D(3)-binding protein-derived macrophage activating factor (GcMAF) on angiogenesis", J Natl Cancer Inst., Sep. 2002, vol. 94, No. 17, pp. 1311-1319.

Mohamad et al., "Preparation of Gc protein-derived macrophage activating factor (GcMAF) and its structural characterization and biological activities", Anticancer Res., Nov. 2002, vol. 22, No. 6C, pp. 4297-4300.

Kisker et al., "Vitamin D binding protein-macrophage activating factor (DBP-maf) inhibits angiogenesis and tumor growth in mice", Neoplasia, Jan. 2003, vol. 5, No. 1, pp. 32-40.

Gumireddy et al., "Mitogen-activated protein kinase pathway mediates DBP-maf-induced apoptosis in RAW 264.7 macrophages", J Cell Biochem., Sep. 2003, vol. 90, No. 1, pp. 87-96.

Mohamad et al., "Gc protein-derived macrophage activating factor (GcMAF): isoelectric focusing pattern and tumoricidal activity", Anticancer Res., Nov. 2003, vol. 23, No. 6a, pp. 4451-4457.

Yamamoto et al., "Immunotherapy for Prostate Cancer with GcMAF", Transl Oncol., Jul. 2008, vol. 1, No. 2, pp. 65-72.

Matsuura et al., "Effect of salivary gland adenocarcinoma cell-derived alpha-N-acetylgalactosaminidase on the bioactivity of macrophage activating factor", Int J Oncol., Mar. 2004, vol. 24, No. 3, pp. 521-528.

Onizuka et al., "Pancreatic Carcinogenesis: Apoptosis and Angiogenesis", Pancreas, Apr. 2004, vol. 28, No. 3, pp. 317-319.

Nagasawa et al., "Association of the macrophage activating factor (MAF) precursor activity with polymorphism in vitamin D-binding protein", Anticancer Res., 2004, vol. 24, No. 5C, pp. 3361-3366.

Nagasawa et al., "Gc protein (vitamin D-binding protein): Gc genotyping and GcMAF precursor activity", Anticancer Res., 2005, vol. 25, No. 6A, pp. 3689-3696.

Kalkunte et al., "Inhibition of angiogenesis by vitamin D-binding protein: characterization of anti-endothelial activity of DBP-maf", Angiogenesis, 2005, vol. 8, No. 4, pp. 349-360.

Bogani et al., "A designed glycoprotein analogue of Gc-MAF exhibits native-like phagocytic activity", J Am Chem Soc., Jun. 2006, vol. 128, No. 22, pp. 7142-7143.

Ravnsborg et al., "The glycosylation and characterization of the candidate Gc macrophage activating factor", Biochim Biophys Acta., Apr. 2010, vol. 1804, No. 4, pp. 909-917.

Nonaka et al., "Vitamin D binding protein-macrophage activating factor inhibits HCC in SCID mice", J Surg Res., Jan. 2012, vol. 172, No. 1, pp. 116-122.

Gregory et al., "Vitamin D binding protein-macrophage activating factor directly inhibits proliferation, migration, and uPAR expression of prostate cancer cells", PLoS One, Oct. 2010, vol. 18, No. 5(10):e13428.

Pacini et al., "Gc protein-derived macrophage-activating factor (GcMAF) stimulates cAMP formation in human mononuclear cells and inhibits angiogenesis in chick embryo chorionallantoic membrane assay", Cancer Immunol Immunother., Apr. 2011, vol. 60, No. 4, pp. 479-485.

Uto et al., "Effect of the Gc-derived macrophage-activating factor precursor (preGcMAF) on phagocytic activation of mouse peritoneal macrophages", Anticancer Res., Jul. 2011, vol. 31, No. 7, pp. 2489-2492.

Pacini et al., "Effect of paricalcitol and GcMAF on angiogenesis and human peripheral blood mononuclear cell proliferation and signaling", J Nephrol., 2012, vol. 25, No. 4, pp. 577-581.

Pacini et al., "Effects of vitamin D-binding protein-derived macrophage-activating factor on human breast cancer cells", Anticancer Res., Jan. 2012, vol. 32, No. 1, pp. 45-52.

Uto et al., "β-Galactosidase treatment is a common first-stage modification of the three major subtypes of Gc protein to GcMAF", Anticancer Res., Jun. 2012, vol. 32, No. 6, pp. 2359-2364.

Bellone et al., "Vitamin D-binding protein-derived macrophage-activating factor, GcMAF, and prostate cancer", Cancer Immunol Immunother., Dec. 2012, vol. 61, No. 12, pp. 2377-2378.

Toyohara et al., "Inhibitory effect of vitamin D-binding protein-derived macrophage activating factor on DMBA-induced hamster cheek pouch carcinogenesis and its derived carcinoma cell line", Oncol Lett., Jul. 2011, vol. 2, No. 4, pp. 685-691.

Kuchiike et al., "Degalactosylated/desialylated human serum containing GcMAF induces macrophage phagocytic activity and in vivo antitumor activity", Anticancer Res., Jul. 2013, vol. 33, No. 7, pp. 2881-2886.

Hirota et al., "Antitumor effect of degalactosylated gc-globulin on orthotopic grafted lung cancer in mice", Anticancer Res., Jul. 2013, vol. 33, No. 7, pp. 2911-2915.

Inui et al., "Clinical experience of integrative cancer immunotherapy with GcMAF", Anticancer Res., Jul. 2013, vol. 33, No. 7, pp. 2917-2920.

Thyer et al., "A novel role for a major component of the vitamin D axis: vitamin D binding protein-derived macrophage activating factor induces human breast cancer cell apoptosis through stimulation of macrophages", Nutrients, Jul. 2013, vol. 5, No. 7, pp. 2577-2589.

Sayegh et al., "Vitamin D in endometriosis: a causative or confounding factor?", Metabolism, Jan. 2014, vol. 63, No. 1, pp. 32-41.

Thyer et al., "GC protein-derived macrophage-activating factor decreases α-N-acetylgalactosaminidase levels in advanced cancer patients", Oncoimmunology, Aug. 2013, vol. 2, No. 8, e25769.

Siniscalco et al., "The in vitro GcMAF effects on endocannabinoid system transcriptionomics, receptor formation, and cell activity of autism-derived macrophages", J Neuroinflammation, Apr. 2014, vol. 11, No. 78, 11 pages.

(56) References Cited

OTHER PUBLICATIONS

Ruggiero et al., "Oleic Acid, deglycosylated vitamin D-binding protein, nitric oxide: a molecular triad made lethal to cancer.", Anticancer Res., Jul. 2014, vol. 34, No. 7, pp. 3569-3578.
Ishikawa et al., "A novel assay system for macrophage-activating factor activity using a human U937 cell line", Anticancer Res., Aug. 2014, vol. 34, No. 8, pp. 4577-4582.
Inui et al., "Case report: A breast cancer patient treated with GcMAF, sonodynamic therapy and hormone therapy", Anticancer Res., Aug. 2014, vol. 34, No. 8, pp. 4589-4594.
Morucci et al., "Gc-protein-derived macrophage activating factor counteracts the neuronal damage induced by oxaliplatin", Anticancer Drugs., Feb. 2015, vol. 26, No. 2, pp. 197-209.
Branca et al., "Effects of oxaliplatin and oleic acid Gc-protein-derived macrophage-activating factor on murine and human microglia", J Neurosci Res., Sep. 2015, vol. 93, No. 9, pp. 1364-1377.
Inui et al., "Oral Colostrum Macrophage-activating Factor for Serious Infection and Chronic Fatigue Syndrome: Three Case Reports", Anticancer Res., Aug. 2015, vol. 35, No. 8, pp. 4545-4550.
Delanghe et al., "Behind the scenes of vitamin D binding protein: more than vitamin D binding", Best Pract Res Clin Endocrinol Metab., Oct. 2015, vol. 29, No. 5, pp. 773-786.
Daiger et al., "Group-specific component (Gc) proteins bind vitamin D and 25-hydroxyvitamin D", Proc. Natl. Acad. Sci. USA, Jun. 1975, vol. 72, No. 6, pp. 2076-2080.
Hamilton et al., "Small cell lung cancer: Recruitment of macrophages by circulating tumor cells", Oncoimmunology, Oct. 2015, vol. 5, No. 3, e1093277.
Inui et al., "Case Report: A Non-small Cell Lung Cancer Patient Treated with GcMAF, Sonodynamic Therapy and Tumor Treating Fields", Anticancer Res., Jul. 2016, vol. 36, No. 7, pp. 3767-3770.
Inui et al., "Case Report: GcMAF Treatment in a Patient with Multiple Sclerosis", Anticancer Res., Jul. 2016, vol. 36, No. 7, pp. 3771-3774.
Borges et al., "Glycan structure of Gc Protein-derived Macrophage Activating Factor as revealed by mass spectrometry", Arch Biochem Biophys., Sep. 2016, vol. 606, pp. 167-179.
Ruggiero et al., "Is chondroitin sulfate responsible for the biological effects attributed to the GC protein-derived Macrophage Activating Factor (GcMAF)?", Med Hypotheses, Sep. 2016, vol. 94, pp. 126-131.
Saburi et al., "Is α-N-acetylgalactosaminidase the key to curing cancer? A mini-review and hypothesis", J Buon, Nov. 2017, vol. 22, No. 6, pp. 1372-1377.
Bakunina et al., "The Effect of Fucoidan from the Brown Alga Fucus evanescence on the Activity of α-N-Acetylgalactosaminidase of Human Colon Carcinoma Cells", Mar Drugs, May 2018, vol. 16, No. 5, pp. E155.
Chun et al., "New perspectives on the vitamin D binding protein", Cell biochemistry and function, Aug. 2012, vol. 30, pp. 445-456.
Thomas et al., Studies on the anti-ricketic activity in sera from patients with disorders of calcium metabolism and preliminary observations on the mode of in human serum, J. Clin. Invest., Jul. 1959, vol. 38, No. 7, pp. 1078-1085.
Cleve et al., "The mutants of the vitamin-D-binding protein: more than 120 variants of the GC/DBP system", Vox. Sang., 1988, vol. 54, pp. 215-225.
Speeckaert et al., "Biological and clinical aspects of the vitamin D binding protein (Gc-globulin) and its polymorphism", Clin. Chim. Acta., Oct. 2006, vol. 372, Nos. 1-2, pp. 33-42.
Borges et al., "Full-length characterization of proteins in human populations", Clin. Chem., Feb. 2010, vol. 56, No. 2, pp. 202-211.

Haddad et al., "Identification of the sterol- and actin-binding domains of plasma vitamin D binding protein (Gc-globulin)", Biochemistry., Aug. 1992, vol. 31, pp. 7174-7181.
Verboven et al., "A structural basis for the unique binding features of the human vitamin D-binding protein", Nat. Struct. Biol., Feb. 2002, vol. 2, pp. 131-136.
Lind et al., "Role of plasma gelsolin and the vitamin D-binding protein in clearing actin from the circulation", J. Clin. Invest., Sep. 1986, vol. 78, No. 3, pp. 736-742.
Lee et al., "The extracellular actin-scavenger system and actin toxicity", N. Engl. J. Med., May 1992, vol. 326, No. 20, pp. 1335-1341.
DiMartion et al., "Initial characterization of the vitamin D binding protein (Gc-globulin) binding site on the neutrophil plasma membrane: evidence for a chondroitin sulfate proteoglycan", J Immunol., Aug. 1999, vol. 63, No. 4, pp. 2135-2142.
McVoy et al., "CD44 and annexin A2 mediate the C5a chemotactic cofactor function of the vitamin D binding protein", J Immunol., Oct. 2005, vol. 175, No. 7, pp. 4754-4760.
Borges et al., "Population studies of vitamin d binding protein microheterogeneity by mass spectrometry lead to characterization of its genotype-dependent O-glycosylation patterns", J. Proteom. Res., Sep. 2008, vol. 7, No. 9, pp. 4143-4153.
Yamamoto et al., "Conversion of vitamin D3 binding protein (group specific component) to a macrophage-activating factor by the stepwise action of betagalactosidase of B-cells and sialidase of T-cells", J Immunol., Sep. 1993, vol. 151, No. 5, pp. 2794-2802.
Abbas et al., "The Gc2 allele of the vitamin D binding protein is associated with a decreased postmenopausal breast cancer risk, independent of the vitamin D status", Cancer Epidemiol. Biomarkers Prev., Jun. 2008, vol. 17, No. 6, pp. 1339-1343.
Link et al., "Purification of human serum vitamin D-binding protein by 25-hydroxyvitamin D3-sepharose chromatography", Anal. Biochem., 1986, vol. 157, pp. 262-269.
Viau et al., "Isolation and Characterization of the O-glycan Chain of the Human vitamin-D Binding Protein", Biochem Biophys Res Commun., Nov. 1983, vol. 117, No. 1, pp. 324-331.
Borges et al., "Population Studies of Intact Vitamin D Binding Protein by Affinity Capture ESI-TOF-MS", J Biomol Tech., Jul. 2008, vol. 19, No. 3, pp. 167-176.
Kilpatrick et al., "Optimizing High-Resolution Mass Spectrometry for the Identification of Low-Abundance Post-Translational Modifications of Intact Proteins", J Proteome Res., Sep. 2017, vol. 16, No. 9, pp. 3255-3265.
Yamamoto et al., "Immunotherapy of Metastatic Breast Cancer Patients With Vitamin D-binding Protein-Derived Macrophage Activating Factor (GcMAF)", Int J Cancer, Jan. 2008, vol. 122, No. 2, pp. 461-467.
Yamamoto et al., "Immunotherapy of Metastatic Colorectal Cancer With Vitamin D-binding Protein-Derived Macrophage-Activating Factor, GcMAF", Cancer Immunol Immunother., Jul. 2008, vol. 57, No. 7, pp. 1007-1106.
Yamamoto et al., "Immunotherapy of HIV-infected Patients With Gc Protein-Derived Macrophage Activating Factor (GcMAF)", J Med Virol., Jan. 2009, vol. 81, No. 1, pp. 16-26.
Phillips et al., "Purified Umbilical Cord Derived Mesenchymal Stem Cell Treatment in a Case of Systemic Lupus Erythematosus", Clin Transl Med., Dec. 2017, vol. 6, No. 31, 4 pages.
Wielders et al., "Automated competitive protein-binding assay for total 25-OH vitamin D, multicenter evaluation and practical performance", J. Clin. Lab. Anal., 2015., vol. 29, pp. 451-461.
Extended European Search Report issued Oct. 5, 2021 in European Patent Application No. 18889081.8.
Jain, Nina K. et al., "A high density CHO-S transient transfection system: Comparison of ExpiCHO and Expi293", Protein Expression and Purification, Mar. 23, 2017, vol. 134, pp. 38-46, XP55839854.

* cited by examiner

SEQUENCE LISTING

```
<160> NUMBER OF SEQ ID NOS: 15

<210> SEQ ID NO 1
<211> LENGTH: 1425
<212> TYPE: DNA
<213> ORGANISM: Homo sapiens

<400> SEQUENCE: 1
atgaagaggg tcctggtact actgcttgct gtggcatttg gacatgcttt agagagaggc    60
cgggattatg aaaagaataa agtctgcaag gaattctccc atctgggaaa ggaggacttc   120
acatctctgt cactagtcct gtacagtaga aaatttccca gtggcacgtt tgaacaggtc   180
agccaacttg tgaaggaagt tgtctccttg accgaagcct gctgtgcgga aggggctgac   240
cctgactgct atgacaccag gacctcagca ctgtctgcca agtcctgtga aagtaattct   300
ccattccccg ttcacccagg cactgctgag tgctgcacca aagagggcct ggaacgaaag   360
```

| | | | |
|---|---|---|---|
| ctctgcatgg | ctgctctgaa | acaccagcca | caggaattcc ctacctacgt ggaacccaca | 420 |
| aatgatgaaa | tctgtgaggc | gttcaggaaa | gatccaaagg aatatgctaa tcaatttatg | 480 |
| tgggaatatt | ccactaatta | cgaacaagct | cctctgtcac ttttagtcag ttacaccaag | 540 |
| agttatcttt | ctatggtagg | gtcctgctgt | acctctgcaa gcccaactgt atgcttttg | 600 |
| aaagagagac | tccagcttaa | acatttatca | cttctcacca ctctgtcaaa tagagtctgc | 660 |
| tcacaatatg | ctgcttatgg | ggagaagaaa | tcaaggctca gcaatctcat aaagttagcc | 720 |
| caaaagtgc | ctactgctga | tctggaggat | gttttgccac tagctgaaga tattactaac | 780 |
| atcctctcca | aatgctgtga | gtctgcctct | gaagattgca tggccaaaga gctgcctgaa | 840 |
| cacacagtaa | aactctgtga | caatttatcc | acaagaatt ctaagtttga agactgttgt | 900 |
| caagaaaaaa | cagccatgga | cgttttgtg | tgcacttact tcatgccagc tgcccaactc | 960 |
| cccgagcttc | cagatgtaag | attgcccaca | aacaaagatg tgtgtgatcc aggaaacacc | 1020 |
| aaagtcatgg | ataagtatac | atttgaacta | agcagaagga ctcatcttcc ggaagtattc | 1080 |
| ctcagtaagg | tacttgagcc | aaccctaaaa | agccttggtg aatgctgtga tgttgaagac | 1140 |
| tcaactacct | gttttaatgc | taagggcccct | ctactaaaga aggaactatc ttctttcatt | 1200 |
| gacaagggac | aagaactatg | tgcagattat | tcagaaaata catttactga gtacaagaaa | 1260 |
| aaactggcag | agcgactaaa | agcaaaattg | cctgatgcca cacccacgga actggcaaag | 1320 |
| ctggttaaca | agcactcaga | ctttgcctcc | aactgctgtt ccataaactc acctcctctt | 1380 |
| tactgtgatt | cagagattga | tgctgaattg | aagaatatcc tgtag | 1425 |

```
<210> SEQ ID NO 2
<211> LENGTH: 1425
<212> TYPE: DNA
<213> ORGANISM: Homo sapiens

<400> SEQUENCE: 2
```

| | | | |
|---|---|---|---|
| atgaagaggg | tcctggtact | actgcttgct | gtggcatttg gacatgcttt agagagaggc | 60 |
| cgggattatg | aaaagaataa | agtctgcaag | gaattctccc atctgggaaa ggaggacttc | 120 |
| acatctctgt | cactagtcct | gtacagtaga | aaatttccca gtggcacgtt tgaacaggtc | 180 |
| agccaacttg | tgaaggaagt | tgtctccttg | accgaagcct gctgtgcgga aggggctgac | 240 |
| cctgactgct | atgacaccag | gacctcagca | ctgtctgcca gtcctgtga aagtaattct | 300 |
| ccattccccg | ttcacccagg | cactgctgag | tgctgcacca agagggcct ggaacgaaag | 360 |
| ctctgcatgg | ctgctctgaa | acaccagcca | caggaattcc ctacctacgt ggaacccaca | 420 |
| aatgatgaaa | tctgtgaggc | gttcaggaaa | gatccaaagg aatatgctaa tcaatttatg | 480 |
| tgggaatatt | ccactaatta | cgaacaagct | cctctgtcac ttttagtcag ttacaccaag | 540 |
| agttatcttt | ctatggtagg | gtcctgctgt | acctctgcaa gcccaactgt atgcttttg | 600 |
| aaagagagac | tccagcttaa | acatttatca | cttctcacca ctctgtcaaa tagagtctgc | 660 |
| tcacaatatg | ctgcttatgg | ggagaagaaa | tcaaggctca gcaatctcat aaagttagcc | 720 |
| caaaagtgc | ctactgctga | tctggaggat | gttttgccac tagctgaaga tattactaac | 780 |
| atcctctcca | aatgctgtga | gtctgcctct | gaagattgca tggccaaaga gctgcctgaa | 840 |
| cacacagtaa | aactctgtga | caatttatcc | acaagaatt ctaagtttga agactgttgt | 900 |
| caagaaaaaa | cagccatgga | cgttttgtg | tgcacttact tcatgccagc tgcccaactc | 960 |
| cccgagcttc | cagatgtaag | attgcccaca | aacaaagatg tgtgtgatcc aggaaacacc | 1020 |

```
aaagtcatgg ataagtatac atttgaacta agcagaagga ctcatcttcc ggaagtattc    1080
ctcagtaagg tacttgagcc aaccctaaaa agccttggtg aatgctgtga tgttgaagac    1140
tcaactacct gttttaatgc taagggccct ctactaaaga aggaactatc ttctttcatt    1200
gacaagggac aagaactatg tgcagattat tcagaaaata catttactga gtacaagaaa    1260
aaactggcag agcgactaaa agcaaaattg cctgaggcca cacccacgga actggcaaag    1320
ctggttaaca agcactcaga ctttgcctcc aactgctgtt ccataaactc acctcctctt    1380
tactgtgatt cagagattga tgctgaattg aagaatatcc tgtag                    1425

<210> SEQ ID NO 3
<211> LENGTH: 1425
<212> TYPE: DNA
<213> ORGANISM: Homo sapiens

<400> SEQUENCE: 3
atgaagaggg tcctggtact actgcttgct gtggcatttg gacatgcttt agagagaggc      60
cgggattatg aaaagaataa agtctgcaag gaattctccc atctgggaaa ggaggacttc     120
acatctctgt cactagtcct gtacagtaga aaatttccca gtggcacgtt gaacaggtc      180 agccaacttg tgaaggaagt tgtctccttg accgaagcct gctgtgcgga agggctgac      240 cctgactgct atgacaccag gacctcagca ctgtctgcca gtcctgtga aagtaattct      300 ccattccccg ttcacccagg cactgctgag tgctgcacca agagggcct ggaacgaaag     360 ctctgcatgg ctgctctgaa acaccagcca caggaattcc ctacctacgt ggaacccaca     420
aatgatgaaa tctgtgaggc gttcaggaaa gatccaaagg aatatgctaa tcaatttatg     480
tgggaatatt ccactaatta cggacaagct cctctgtcac ttttagtcag ttacaccaag     540
agttatcttt ctatggtagg gtcctgctgt acctctgcaa gcccaactgt atgcttttg      600 aaagagagac tccagcttaa acatttatca cttctcacca ctctgtcaaa tagagtctgc     660
tcacaatatg ctgcttatgg ggagaagaaa tcaaggctca gcaatctcat aaagttagcc     720
caaaaagtgc ctactgctga tctggaggat gttttgccac tagctgaaga tattactaac     780
atcctctcca atgctgtgaa gtctgcctct gaagattgca tggccaaaga gctgcctgaa     840
cacacagtaa aactctgtga caatttatcc acaagaatt ctaagtttga agactgttgt      900
caagaaaaaa cagccatgga cgttttgtg tgcacttact tcatgccagc tgcccaactc      960
cccgagcttc cagatgtaga gttgcccaca acaaagatg tgtgtgatcc aggaaacacc    1020
aaagtcatgg ataagtatac atttgaacta agcagaagga ctcatcttcc ggaagtattc    1080
ctcagtaagg tacttgagcc aaccctaaaa agccttggtg aatgctgtga tgttgaagac    1140
tcaactacct gttttaatgc taagggccct ctactaaaga aggaactatc ttctttcatt    1200
gacaagggac aagaactatg tgcagattat tcagaaaata catttactga gtacaagaaa    1260
aaactggcag agcgactaaa agcaaaattg cctgatgcca cacccaagga actggcaaag    1320
ctggttaaca agcactcaga ctttgcctcc aactgctgtt ccataaactc acctcctctt    1380
tactgtgatt cagagattga tgctgaattg aagaatatcc tgtag                    1425

<210> SEQ ID NO 4
<211> LENGTH: 474
<212> TYPE: PRT
<213> ORGANISM: Homo sapiens

<400> SEQUENCE: 4

Met Lys Arg Val Leu Val Leu Leu Leu Ala Val Ala Phe Gly His Ala
```

```
1               5                   10                  15
Leu Glu Arg Gly Arg Asp Tyr Glu Lys Asn Lys Val Cys Lys Glu Phe
                20                  25                  30
Ser His Leu Gly Lys Glu Asp Phe Thr Ser Leu Ser Leu Val Leu Tyr
                35                  40                  45
Ser Arg Lys Phe Pro Ser Gly Thr Phe Glu Gln Val Ser Gln Leu Val
        50                  55                  60
Lys Glu Val Val Ser Leu Thr Glu Ala Cys Cys Ala Glu Gly Ala Asp
65                  70                  75                  80
Pro Asp Cys Tyr Asp Thr Arg Thr Ser Ala Leu Ser Ala Lys Ser Cys
                85                  90                  95
Glu Ser Asn Ser Pro Phe Pro Val His Pro Gly Thr Ala Glu Cys Cys
                100                 105                 110
Thr Lys Glu Gly Leu Glu Arg Lys Leu Cys Met Ala Ala Leu Lys His
                115                 120                 125
Gln Pro Gln Glu Phe Pro Thr Tyr Val Glu Pro Thr Asn Asp Glu Ile
                130                 135                 140
Cys Glu Ala Phe Arg Lys Asp Pro Lys Glu Tyr Ala Asn Gln Phe Met
145                 150                 155                 160
Trp Glu Tyr Ser Thr Asn Tyr Glu Gln Ala Pro Leu Ser Leu Leu Val
                165                 170                 175
Ser Tyr Thr Lys Ser Tyr Leu Ser Met Val Gly Ser Cys Cys Thr Ser
                180                 185                 190
Ala Ser Pro Thr Val Cys Phe Leu Lys Glu Arg Leu Gln Leu Lys His
                195                 200                 205
Leu Ser Leu Leu Thr Thr Leu Ser Asn Arg Val Cys Ser Gln Tyr Ala
                210                 215                 220
Ala Tyr Gly Glu Lys Lys Ser Arg Leu Ser Asn Leu Ile Lys Leu Ala
225                 230                 235                 240
Gln Lys Val Pro Thr Ala Asp Leu Glu Asp Val Leu Pro Leu Ala Glu
                245                 250                 255
Asp Ile Thr Asn Ile Leu Ser Lys Cys Cys Glu Ser Ala Ser Glu Asp
                260                 265                 270
Cys Met Ala Lys Glu Leu Pro Glu His Thr Val Lys Leu Cys Asp Asn
                275                 280                 285
Leu Ser Thr Lys Asn Ser Lys Phe Glu Asp Cys Cys Gln Glu Lys Thr
                290                 295                 300
Ala Met Asp Val Phe Val Cys Thr Tyr Phe Met Pro Ala Ala Gln Leu
305                 310                 315                 320
Pro Glu Leu Pro Asp Val Arg Leu Pro Thr Asn Lys Asp Val Cys Asp
                325                 330                 335
Pro Gly Asn Thr Lys Val Met Asp Lys Tyr Thr Phe Glu Leu Ser Arg
                340                 345                 350
Arg Thr His Leu Pro Glu Val Phe Leu Ser Lys Val Leu Glu Pro Thr
                355                 360                 365
Leu Lys Ser Leu Gly Glu Cys Cys Asp Val Glu Asp Ser Thr Thr Cys
                370                 375                 380
Phe Asn Ala Lys Gly Pro Leu Leu Lys Lys Glu Leu Ser Ser Phe Ile
385                 390                 395                 400
Asp Lys Gly Gln Glu Leu Cys Ala Asp Tyr Ser Glu Asn Thr Phe Thr
                405                 410                 415
Glu Tyr Lys Lys Lys Leu Ala Glu Arg Leu Lys Ala Lys Leu Pro Asp
                420                 425                 430
```

```
Ala Thr Pro Thr Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 5
<211> LENGTH: 474
<212> TYPE: PRT
<213> ORGANISM: Homo sapiens

<400> SEQUENCE: 5

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
```

```
            325                 330                 335
Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
            355                 360                 365

Leu Lys Ser Leu Gly Glu Cys Cys Asp Val Glu Asp Ser Thr Thr Cys
            370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
            405                 410                 415

Glu Tyr Lys Lys Lys Leu Ala Glu Arg Leu Lys Ala Lys Leu Pro Glu
            420                 425                 430

Ala Thr Pro Thr Glu Leu Ala Lys Leu Val Asn Lys His Ser Asp Phe
            435                 440                 445

Ala Ser Asn Cys Cys Ser Ile Asn Ser Pro Pro Leu Tyr Cys Asp Ser
            450                 455                 460

Glu Ile Asp Ala Glu Leu Lys Asn Ile Leu
465                 470

<210> SEQ ID NO 6
<211> LENGTH: 474
<212> TYPE: PRT
<213> ORGANISM: Homo sapiens

<400> SEQUENCE: 6

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
            35                  40                  45

Ser Arg Lys Phe Pro Ser Gly Thr Phe Glu Gln Val Ser Gln Leu Val
50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
            115                 120                 125

Gln Pro Gln Glu Phe Pro Thr Tyr Val Glu Pro Thr Asn Asp Glu Ile
            130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
            195                 200                 205

Leu Ser Leu Leu Thr Thr Leu Ser Asn Arg Val Cys Ser Gln Tyr Ala
            210                 215                 220
```

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
            245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
            325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
            405                 410                 415

Glu Tyr Lys Lys Lys Leu Ala Glu Arg Leu Lys Ala Lys Leu Pro Asp
            420                 425                 430

Ala Thr Pro Lys Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 7
<211> LENGTH: 1425
<212> TYPE: DNA
<213> ORGANISM: Homo sapiens

<400> SEQUENCE: 7
atgaagcggg tgctggtgct gctgctggcc gtggcctttg acacgccct ggaaagaggc      60 cgggactacg agaagaacaa agtgtgcaaa gagttcagcc acctgggcaa agaggacttc     120
accagcctga cctggtgct gtacagccgg aagttcccca gcggcacctt cgaacaggtg     180
tcccagctgg tcaaagaagt ggtgtccctg accgaggcct gttgcgccga aggcgccgac    240
cctgactgct acgataccag aacaagcgcc ctgagcgcca agagctgcga gagcaacagc    300 cccttcctg tgcaccctgg caccgccgag tgctgcacaa agagggcct ggaacggaag      360 ctgtgcatgg ccgccctgaa gcaccagccc caggaattcc ctacctacgt cgagcccacc    420
aacgacgaga tttgcgaggc cttcagaaag accccaaag agtacgccaa ccagttcatg    480
tgggagtaca gcaccaacta cgagcaggcc cccctgagcc tgctggtgtc ctacaccaag    540
agctacctga gcatggtcgg aagctgctgc accagcgcca gcctaccgt gtgcttcctg    600 aaagagcggc tgcagctgaa gcacctgtcc ctgctgacca ccctgagcaa cagagtgtgc    660
agccagtacg ccgcctacgg cgagaagaag tcccggctga gcaacctgat caagctggcc    720

-continued

```
cagaaggtgc ccaccgccga cctggaagat gtgctgcctc tggccgagga catcaccaac    780
atcctgagca agtgctgcga gtccgccagc gaggactgca tggccaaaga gctgcccgag    840
cacaccgtga agctgtgcga caacctgagc accaagaaca gcaagttcga ggactgctgc    900
caggaaaaga ccgccatgga cgtgttcgtg tgcacctact tcatgcctgc cgcccagctg    960
cctgagctgc agatgtgcg gctgcccacc aacaaggacg tgtgcgaccc cggcaacacc   1020
aaagtgatgg acaagtacac cttcgagctg agccggcgga cccatctgcc cgaagtgttt   1080
ctgtccaagg tgctggaacc caccctgaag tccctgggcg agtgctgcga cgtggaagat   1140
agcaccacct gtttcaacgc caagggcccc ctgctgaaga aagagctgag cagcttcatc   1200
gacaagggcc aggaactgtg cgccgactac agcgagaaca ccttcaccga gtacaagaag   1260
aagctggccg agcggctgaa ggccaagctg cctgatgcca cacctaccga gctggccaag   1320
ctggtcaaca gcggagcga cttcgccagc aactgctgca gcatcaacag ccccccactg   1380
tactgcgaca gcgagatcga cgccgagctg aagaacatcc tgtag                  1425
```

<210> SEQ ID NO 8
<211> LENGTH: 474
<212> TYPE: PRT
<213> ORGANISM: Homo sapiens

<400> SEQUENCE: 8

```
Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
```

```
                245                 250                 255
Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys Arg Ser Asp Phe
        435                 440                 445

Ala Ser Asn Cys Cys Ser Ile Asn Ser Pro Pro Leu Tyr Cys Asp Ser
    450                 455                 460

Glu Ile Asp Ala Glu Leu Lys Asn Ile Leu
465                 470

<210> SEQ ID NO 9
<211> LENGTH: 1458
<212> TYPE: DNA
<213> ORGANISM: Homo sapiens

<400> SEQUENCE: 9
atgaagcggg tgctggtgct gctgctggcc gtggcctttg acacgcccct ggaaagaggc      60
cgggactacg agaagaacaa agtgtgcaaa gagttcagcc acctgggcaa agaggacttc     120
accagcctga gcctggtgct gtacagccgg aagttcccca gcggcacctt cgaacaggtg     180
tcccagctgg tcaaagaagt ggtgtccctg accgaggcct gttgcgccga aggcgccgac     240
cctgactgct acgataccag aacaagcgcc ctgagcgcca gagctgcga gagcaacagc     300
cccttcctg tgcaccctgg caccgccgag tgctgcacaa agagggcct ggaacggaag     360
ctgtgcatgg ccgccctgaa gcaccagccc aggaattcc ctacctacgt cgagcccacc     420
aacgacgaga tttgcgaggc cttcagaaag accccaaag agtacgccaa ccagttcatg     480
tgggagtaca gcaccaacta cgagcaggcc cccctgagcc tgctggtgtc ctacaccaag     540
agctacctga gcatggtcgg aagctgctgc accagcgcca ccctaccgt gtgcttcctg     600
aaagagcggc tgcagctgaa gcacctgtcc ctgctgacca ccctgagcaa cagagtgtgc     660
agccagtacg ccgcctacgg cgagaagaag tcccggctga gcaacctgat caagctggcc     720
cagaaggtgc ccaccgccga cctggaagat gtgctgcctc tggccgagga catcaccaac     780
atcctgagca gtgctgcga gtccgccagc gaggactgca tggccaaaga gctgcccgag     840
```

```
cacaccgtga agctgtgcga caacctgagc accaagaaca gcaagttcga ggactgctgc    900
caggaaaaga ccgccatgga cgtgttcgtg tgcacctact tcatgcctgc cgcccagctg    960
cctgagctgc cagatgtgcg gctgcccacc aacaaggacg tgtgcgaccc cggcaacacc   1020
aaagtgatgg acaagtacac cttcgagctg agccggcgga cccatctgcc cgaagtgttt   1080
ctgtccaagg tgctggaacc caccctgaag tccctgggcg agtgctgcga cgtggaagat   1140
agcaccacct gtttcaacgc caagggcccc ctgctgaaga aagagctgag cagcttcatc   1200
gacaagggcc aggaactgtg cgccgactac agcgagaaca ccttcaccga gtacaagaag   1260
aagctggccg agcggctgaa ggccaagctg cctgatgcca cacctaccga gctggccaag   1320
ctggtcaaca gcggagcga cttcgccagc aactgctgca gcatcaacag ccccccactg   1380
tactgcgaca gcgagatcga cgccgagctg aagaacatcc tgcaccacca ccatcaccat   1440
catcaccacc attgatga                                                 1458
```

<210> SEQ ID NO 10
<211> LENGTH: 1428
<212> TYPE: DNA
<213> ORGANISM: Homo sapiens

<400> SEQUENCE: 10

```
atgaagcggg tgctggtgct gctgctggcc gtggcctttg acacgccct ggaaagaggc      60 cgggactacg agaagaacaa agtgtgcaaa gagttcagcc acctgggcaa agaggacttc    120
accagcctga gcctggtgct gtacagccgg aagttcccca gcggcacctt cgaacaggtg    180
tcccagctgg tcaaagaagt ggtgtccctg accgaggcct gttgcgccga aggcgccgac    240
cctgactgct acgataccag aacaagcgcc ctgagcgcca agagctgcga gagcaacagc    300 cccttcctg tgcaccctgg caccgccgag tgctgcacaa agagggcct ggaacggaag    360 ctgtgcatgg ccgccctgaa gcaccagccc aggaattcc ctacctacgt cgagcccacc    420
aacgacgaga tttgcgaggc cttcagaaag gaccccaaag agtacgccaa ccagttcatg    480
tgggagtaca gcaccaacta cgagcaggcc cccctgagcc tgctggtgtc ctacaccaag    540
agctacctga gcatggtcgg aagctgctgc accagcgcca gccctaccgt gtgcttcctg    600
aaagagcggc tgcagctgaa gcacctgtcc ctgctgacca ccctgagcaa cagagtgtgc    660
agccagtacg ccgcctacgg cgagaagaag tcccggctga gcaacctgat caagctggcc    720
cagaaggtgc ccaccgccga cctggaagat gtgctgcctc tggccgagga catcaccaac    780
atcctgagca gtgctgcga gtccgccagc gaggactgca tggccaaaga gctgcccgag    840
cacaccgtga agctgtgcga caacctgagc accaagaaca gcaagttcga ggactgctgc    900
caggaaaaga ccgccatgga cgtgttcgtg tgcacctact tcatgcctgc cgcccagctg    960
cctgagctgc cagatgtgcg gctgcccacc aacaaggacg tgtgcgaccc cggcaacacc   1020
aaagtgatgg acaagtacac cttcgagctg agccggcgga cccatctgcc cgaagtgttt   1080
ctgtccaagg tgctggaacc caccctgaag tccctgggcg agtgctgcga cgtggaagat   1140
agcaccacct gtttcaacgc caagggcccc ctgctgaaga aagagctgag cagcttcatc   1200
gacaagggcc aggaactgtg cgccgactac agcgagaaca ccttcaccga gtacaagaag   1260
aagctggccg agcggctgaa ggccaagctg cctgaggcca cacctaccga gctggccaag   1320
ctggtcaaca gcggagcga cttcgccagc aactgctgca gcatcaacag ccccccactg   1380
tactgcgaca gcgagatcga cgccgagctg aagaacatcc tgtgatga                1428
```

<210> SEQ ID NO 11
<211> LENGTH: 474
<212> TYPE: PRT
<213> ORGANISM: Homo sapiens

<400> SEQUENCE: 11

Met Lys Arg Val Leu Val Leu Leu Leu Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Glu Leu Ser Ser Phe Ile
385                 390                 395                 400

Asp Lys Gly Gln Glu Leu Cys Ala Asp Tyr Ser Glu Asn Thr Phe Thr
            405                 410                 415

Glu Tyr Lys Lys Lys Leu Ala Glu Arg Leu Lys Ala Lys Leu Pro Glu
        420                 425                 430

Ala Thr Pro Thr Glu Leu Ala Lys Leu Val Asn Lys Arg Ser Asp Phe
        435                 440                 445

Ala Ser Asn Cys Cys Ser Ile Asn Ser Pro Pro Leu Tyr Cys Asp Ser
        450                 455                 460

Glu Ile Asp Ala Glu Leu Lys Asn Ile Leu
465                 470

<210> SEQ ID NO 12
<211> LENGTH: 1428
<212> TYPE: DNA
<213> ORGANISM: Homo sapiens

<400> SEQUENCE: 12

```
atgaagcggg tgctggtgct gctgctggcc gtggcctttg acacgccct ggaaagaggc      60
cgggactacg agaagaacaa agtgtgcaaa gagttcagcc acctgggcaa agaggacttc    120
accagcctga cctggtgct gtacagccgg aagttcccca gcggcacctt cgaacaggtg    180
tcccagctgg tcaaagaagt ggtgtccctg accgaggcct gttgcgccga aggcgccgac    240
cctgactgct acgataccag aacaagcgcc ctgagcgcca agagctgcga gagcaacagc    300
ccctttcctg tgcaccctgg caccgccgag tgctgcacaa agagggcct ggaacggaag    360
ctgtgcatgg ccgccctgaa gcaccagccc caggaattcc ctacctacgt cgagcccacc    420
aacgacgaga tttgcgaggc cttcagaaag gaccccaaag agtacgccaa ccagttcatg    480
tgggagtaca gcaccaacta cgagcaggcc cccctgagcc tgctggtgtc ctacaccaag    540
agctacctga gcatggtcgg aagctgctgc accagcgcca gccctaccgt gtgcttcctg    600
aaagagcggc tgcagctgaa gcacctgtcc ctgctgacca ccctgagcaa cagagtgtgc    660
agccagtacg ccgcctacgg cgagaagaag tcccggctga gcaacctgat caagctggcc    720
cagaaggtgc ccaccgccga cctggaagat gtgctgcctc tggccgagga catcaccaac    780
atcctgagca agtgctgcga gtccgccagc gaggactgca tggccaaaga gctgcccgag    840
cacaccgtga gctgtgcga caacctgagc accaagaaca gcaagttcga ggactgctgc    900
caggaaaaga ccgccatgga cgtgttcgtg tgcacctact tcatgcctgc cgcccagctg    960
cctgagctgc cagatgtgcg gctgcccacc aacaaggacg tgtgcgaccc cggcaacacc   1020
aaagtgatga caagtacac cttcgagctg agccggcgga cccatctgcc cgaagtgttt   1080
ctgtccaagg tgctggaacc caccctgaag tccctgggcg agtgctgcga cgtggaagat   1140
agcaccacct gtttcaacgc caagggcccc ctgctgaaga aagagctgag cagcttcatc   1200
gacaagggcc aggaactgtg cgccgactac agcgagaaca ccttcaccga gtacaagaag   1260
aagctggccg agcggctgaa ggccaagctg cctgatgcca cacctaagga gctggccaag   1320
ctggtcaaca gcggagcga cttcgccagc aactgctgca gcatcaacag cccccactg   1380
tactgcgaca gcgagatcga cgccgagctg aagaacatcc tgtgatga              1428
```

<210> SEQ ID NO 13
<211> LENGTH: 474
<212> TYPE: PRT

<213> ORGANISM: Homo sapiens

<400> SEQUENCE: 13

Met Lys Arg Val Leu Val Leu Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
50                  55                  60

Lys Glu Val Val Ser Leu Thr Glu Ala Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Glu Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
290                 295                 300

Ala Met Asp Val Phe Val Cys Thr Tyr Phe Met Pro Ala Ala Gln Leu
305                 310                 315                 320

Pro Glu Leu Pro Asp Val Arg Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

```
Asp Lys Gly Gln Glu Leu Cys Ala Asp Tyr Ser Glu Asn Thr Phe Thr
            405                 410                 415
Glu Tyr Lys Lys Lys Leu Ala Glu Arg Leu Lys Ala Lys Leu Pro Asp
        420                 425                 430
Ala Thr Pro Lys Glu Leu Ala Lys Leu Val Asn Lys Arg Ser Asp Phe
    435                 440                 445
Ala Ser Asn Cys Cys Ser Ile Asn Ser Pro Pro Leu Tyr Cys Asp Ser
450                 455                 460
Glu Ile Asp Ala Glu Leu Lys Asn Ile Leu
465                 470

<210> SEQ ID NO 14
<211> LENGTH: 1458
<212> TYPE: DNA
<213> ORGANISM: Homo sapiens

<400> SEQUENCE: 14
atgaagcggg tgctggtgct gctgctggcc gtggcctttg acacgccct ggaaagaggc      60
cgggactacg agaagaacaa agtgtgcaaa gagttcagcc acctgggcaa agaggacttc    120
accagcctga gctggtgct gtacagccgg aagttcccca gcggcacctt cgaacaggtg    180
tcccagctgg tcaaagaagt ggtgtccctg accgaggcct gttgcgccga aggcgccgac   240
cctgactgct acgataccag aacaagcgcc ctgagcgcca agagctgcga gagcaacagc   300
cccttcctg tgcaccctgg caccgccgag tgctgcacaa agagggcct ggaacggaag    360
ctgtgcatgg ccgccctgaa gcaccagccc caggaattcc ctacctacgt cgagcccacc   420
aacgacgaga tttgcgaggc cttcagaaag daccccaaag agtacgccaa ccagttcatg   480
tgggagtaca gcaccaacta cgagcaggcc cccctgagcc tgctggtgtc ctacaccaag   540
agctacctga gcatggtcgg aagctgctgc accagcgcca gcctaccgt gtgcttcctg   600
aaagagcggc tgcagctgaa gcacctgtcc ctgctgacca ccctgagcaa cagagtgtgc   660
agccagtacg ccgcctacgg cgagaagaag tcccggctga gcaacctgat caagctggcc   720
cagaaggtgc ccaccgccga cctggaagat gtgctgcctc tggccgagga catcaccaac   780
atcctgagca agtgctgcga gtccgccagc gaggactgca tggccaaaga gctgcccgag   840
cacaccgtga gctgtgcga caacctgagc accaagaaca gcaagttcga ggactgctgc   900
caggaaaaga ccgccatgga cgtgttcgtg tgcacctact tcatgcctgc cgcccagctg   960
cctgagctgc cagatgtgcg gctgcccacc aacaaggacg tgtgcgaccc cggcaacacc  1020
aaagtgatgg acaagtacac cttcgagctg agccggcgga cccatctgcc cgaagtgttt  1080
ctgtccaagg tgctggaacc caccctgaag tccctgggcg agtgctgcga cgtggaagat  1140
agcaccacct gtttcaacgc caagggcccc ctgctgaaga aagagctgag cagcttcatc  1200
gacaagggcc aggaactgtg cgccgactac agcgagaaca ccttcaccga gtacaagaag  1260
aagctggccg agcggctgaa ggccaagctg cctgaggcca cctaccgg ctgccaag      1320
ctggtcaaca gcggagcga cttcgccagc aactgctgca gcatcaacag ccccccactg    1380
tactgcgaca gcgagatcga cgccgagctg aagaacatcc tgcaccacca ccatcaccat  1440
catcaccacc attgatga                                                  1458

<210> SEQ ID NO 15
<211> LENGTH: 1458
<212> TYPE: DNA
<213> ORGANISM: Homo sapiens
```

```
<400> SEQUENCE: 15
atgaagcggg tgctggtgct gctgctggcc gtggcctttg gacacgccct ggaaagaggc      60
cgggactacg agaagaacaa agtgtgcaaa gagttcagcc acctgggcaa agaggacttc     120
accagcctga gcctggtgct gtacagccgg aagttcccca gcggcacctt cgaacaggtg     180
tcccagctgg tcaaagaagt ggtgtccctg accgaggcct gttgcgccga aggcgccgac    240
cctgactgct acgataccag aacaagcgcc ctgagcgcca agagctgcga gagcaacagc     300 cccttcctg tgcaccctgg caccgccgag tgctgcacaa aagagggcct ggaacggaag      360
ctgtgcatgg ccgccctgaa gcaccagccc caggaattcc ctacctacgt cgagcccacc     420
aacgacgaga tttgcgaggc cttcagaaag gaccccaaag agtacgccaa ccagttcatg     480
tgggagtaca gcaccaacta cgagcaggcc cccctgagcc tgctggtgtc ctacaccaag     540
agctacctga gcatggtcgg aagctgctgc accagcgcca gccctaccgt gtgcttcctg     600
aaagagcggc tgcagctgaa gcacctgtcc ctgctgacca ccctgagcaa cagagtgtgc     660
agccagtacg ccgcctacgg cgagaagaag tcccggctga gcaacctgat caagctggcc     720
cagaaggtgc ccaccgccga cctggaagat gtgctgcctc tggccgagga catcaccaac     780
atcctgagca agtgctgcga gtccgccagc gaggactgca tggccaaaga gctgcccgag     840
cacaccgtga agctgtgcga caacctgagc accaagaaca gcaagttcga ggactgctgc     900
caggaaaaga ccgccatgga cgtgttcgtg tgcacctact tcatgcctgc cgcccagctg     960
cctgagctgc cagatgtgcg gctgcccacc aacaaggacg tgtgcgaccc cggcaacacc    1020
aaagtgatgg acaagtacac cttcgagctg agccggcgga cccatctgcc cgaagtgttt    1080
ctgtccaagg tgctggaacc caccctgaag tccctgggcg agtgctgcga cgtggaagat    1140
agcaccacct gtttcaacgc caagggcccc ctgctgaaga aagagctgag cagcttcatc    1200
gacaagggcc aggaactgtg cgccgactac agcgagaaca ccttcaccga gtacaagaag    1260
aagctggccg agcggctgaa ggccaagctg cctgatgcca cacctaagga gctggccaag    1320
ctggtcaaca gcggagcga cttcgccagc aactgctgca gcatcaacag ccccccactg    1380
tactgcgaca gcgagatcga cgccgagctg aagaacatcc tgcaccacca ccatcaccat    1440
catcaccacc attgatga                                                  1458
```

METHOD FOR PRODUCING ACTIVE GcMAF

TECHNICAL FIELD

The present invention relates to a method for producing active GcMAF.

BACKGROUND ART

A vitamin-D binding protein (VDBP) is one of glycoproteins synthesized in the liver and secreted into the blood. The VDBP binds to vitamin D and plays a role as its transfer carrier in the blood. The VDBP is also known to bind to G-actin, which leaks out from destroyed cells, and play a role in suppressing an actin polymer from narrowing and clogging the vascular lumen. The VDBP is also called as Gc globulin. The VDBP has three subtypes (VDBP1f, VDBP1s, VDBP2) different in part in amino acids and sugar chain structure. Of them, in VDBP1f (Gc1f), a trisaccharide Olinked sugar chain formed by binding sialic acid and galactose to GalNAc is linked to the 418 (420)th threonine. The VDBP containing the trisaccharide O-linked sugar chain is an inactive VDBP, which does not have a function to activate macrophages. However, when sialic acid and galactose are removed by the actions of sialidase and β-galactosidase expressed on the surfaces of T cells and B cells, respectively, and only GalNAc-O-T418 (420) remains, the VDBP is converted into an active form thereof, Gc protein-derived macrophage activating factor (GcMAF, hereinafter sometimes referred to as "active GcMAF"), which can activate macrophages (see, Non Patent Documents 1 and 2). The active form thereof, GcMAF is known not only to activate macrophages but also to exhibit an antitumor activity via an antiangiogenic effect (see, Patent Document 1).

As schematically shown in FIG. 1, the step of converting inactive VDBP into an active form thereof, GcMAF, is complicated. In producing the active GcMAF, a method of purifying inactive VDBP from serum or plasma, and removing sialic acid and galactose by treating the VDBP with sialidase and β-galactosidase, respectively, to leave GalNAc alone is generally employed. However, such a conventional method is complicated because it requires a plurality of steps comprising a step of purifying inactive VDBP from serum or plasma, and a step of treating the obtained VDBP with enzymes. Therefore, a more convenient and easier production method has been desired.

PRIOR ART DOCUMENTS

Patent Document

Patent Document 1: JP 2003-532682 A

Non Patent Document

Non Patent Document 1: Proc. Natl. Acad. Sci. USA 1991, 88, 8539-8543 Non Patent Document 2: Anticancer Research, 2005. 25, 3689-3696

SUMMARY OF INVENTION

Technical Problem

In the circumstances, an object of the present invention is to provide a method for producing active GcMAF more convenient with a high yield.

Solution to Problem

The present inventors conducted intensive studies with a view to attaining the above object. As a result, the inventors found that the active GcMAF having only GalNAc linked with the 418 (420)th threonine can be efficiently produced by culturing host cells transfected with an inactive VDBP expression vector in a serum-free medium, without an enzymatic treatment step for deglycosylation. Based on the finding, the present invention was accomplished. More specifically, the present invention will be summarized as follows.

[1] A method for producing active Gc protein-derived macrophage activating factor (GcMAF), comprising a step of culturing host cells transfected with a vitamin-D binding protein expression vector in a serum-free medium.

[2] The method for producing active GcMAF according to [1], wherein the culture is a suspension culture.

[3] The method for producing active GcMAF according to [1] or [2], comprising no enzymatic treatment step for deglycosylation.

[4] The method for producing active GcMAF according to any one of [1] to [3], comprising a purification step by a vitamin-D affinity column.

Advantageous Effects of Invention

According to the method for producing active GcMAF of the present invention a process of expressing VDBP in cultured cells is employed, and therefore it is not necessary to collect serum, plasma or the like and is also easy to mass-produce the active GcMAF. In addition, it is not necessary to carry out a step of purifying VDBP from serum, plasma or the like, or an enzymatic treatment step for deglycosylation. Therefore, the active GcMAF can be efficiently and conveniently produced in fewer steps. Since the active GcMAF, which has been hardly produced in large quantity, can be easily mass-produced by the present invention, the active GcMAF can be suitably used in the fields such as medicines and healthy foods, as an active ingredient.

DESCRIPTION OF EMBODIMENTS

Now, the method for producing active GcMAF of the present invention will be more specifically described. Note that, in the specification, molecular biology technique, such as preparation of DNA and vectors, can be carried out in accordance with methods described in general biological experimental procedures known to those skilled in the art, or equivalent methods thereto, unless otherwise specified. The terms used in the specification are interpreted as those usually meant in the art, unless otherwise mentioned.

<Method for Producing Active GcMAF>

The method for producing active GcMAF of the present invention includes a step of culturing cells transfected with a VDBP expression vector, in a serum-free medium, and is characterized by requiring no enzymatic treatment step for deglycosylation of inactive VDBP.

The method for producing active GcMAF of the present invention is not a method for producing active GcMAF by purifying Gc globulin from plasma or serum but a method of producing active GcMAF by culturing cells transfected with a VDBP expression vector, in a serum-free medium, conveniently without requiring a plurality of steps.

Figure 1:
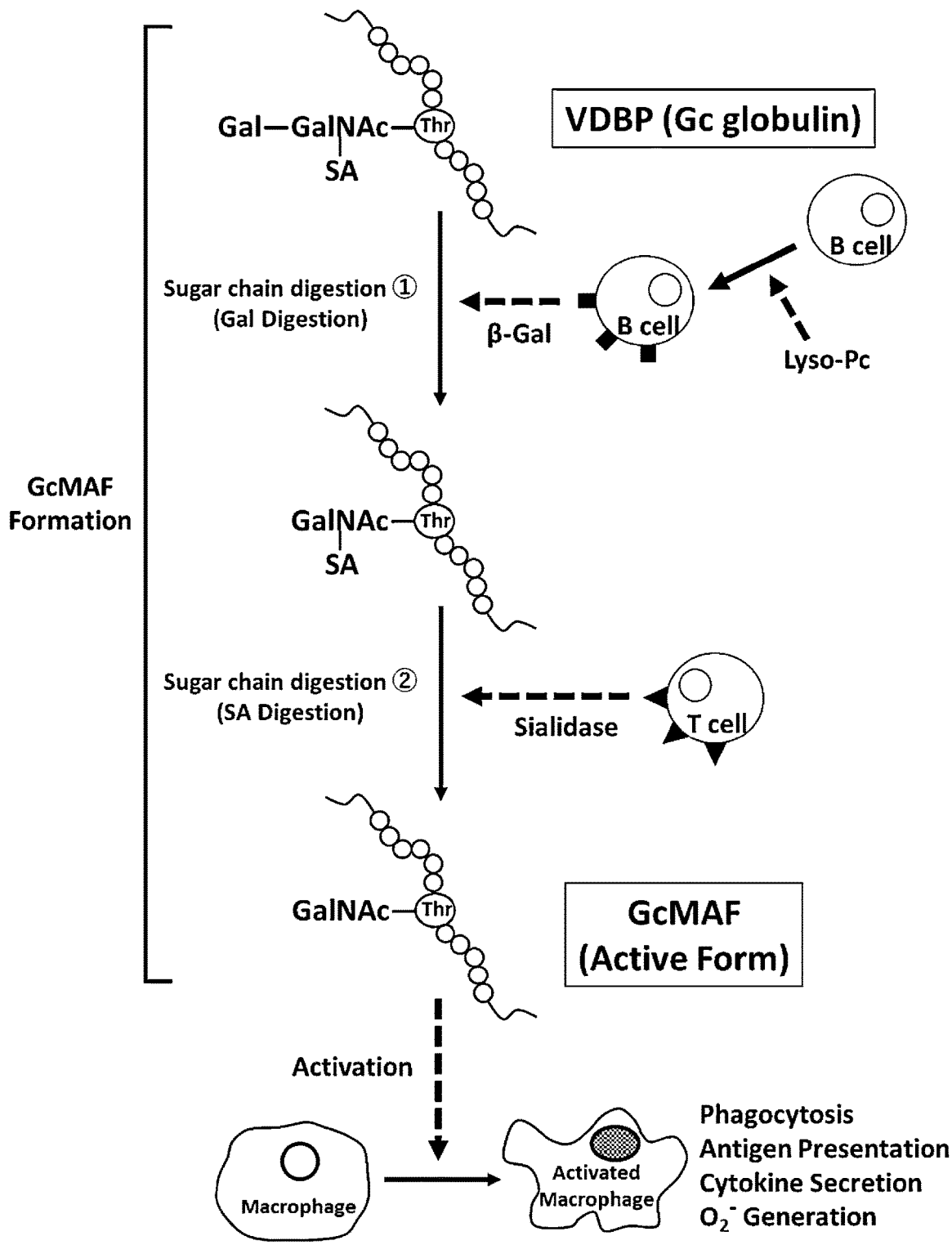
FIG. 1 is a diagram schematically showing steps of converting inactive VDBP into active GcMAF.

In the present invention, VDBP refers to vitamin-D binding protein (VDBP), which is also called as Gc globulin or Gc protein, and has three subtypes (1f, 1s, 2) different in sugar chain structure. All the subtypes of VDBP have a common structure in which galactose is bound to the center of the sugar chain, i.e., N-acetylgalactosamine via an O-glycosidic bond. In subtype 1f, a trisaccharide formed by binding of galactose and sialic acid to GalNAc is O-linked (see, FIG. 1). In subtype 1s, a trisaccharide formed by binding of galactose and α-mannose to GalNAc is O-linked. In subtype 2, a disaccharide formed by binding of Galactose to GalNAc is O-linked. These all VDBP subtypes are included in the present invention. The VDBP of the present invention is derived from animals, preferably derived from mammals such as a human, a horse, a cow, a sheep, a pig, a dog, a cat, a rabbit, a mouse and a rat. Among them, the VDBP derived from a human is more preferable.

A VDBP expression vector of the present invention is prepared by artificially inserting a nucleic acid encoding VDBP into an appropriate expression vector by use of a gene recombination technique. According to the method for producing active GcMAF of the present invention, the active GcMAF can be efficiently produced by allowing the expression vector to express in appropriate host cells and culturing the host cells under appropriate culture conditions, without carrying out an enzymatic treatment for deglycosylation of inactive VDBP. Note that, the amino acid sequence and nucleic acid sequence of VDBP are known and sequence information registered in a database such as GenBank can be used.

The VDBP expression vector of the present invention may be an expression vector in which a nucleic acid encoding any of the subtypes, VDBP1f, VDBP1s and VDBP2 is inserted; and in particular, a VDBP1f expression vector in which a nucleic acid encoding VDBP1f is inserted and a VDBP1s expression vector in which a nucleic acid encoding VDBP1s is inserted are preferable, and the VDBP1f expression vector is more preferable. The nucleic acid sequences encoding VDBP1f, VDBP1s and VDBP2 are shown as SEQ ID No. 1, SEQ ID No. 2 and SEQ ID No. 3, respectively, in the sequence listing. The amino acid sequences of VDBP1f, VDBP1s and VDBP2 are shown as SEQ ID No. 4, SEQ ID No. 5 and SEQ ID No. 6, respectively. As the nucleic acid sequence to be inserted into a VDBP expression vector, a sequence with an optimized translation activity is preferable, and the optimized nucleic acid sequence of VDBP1f is shown as SEQ ID No. 7 and the amino acid sequence corresponding thereto is shown as SEQ ID No. 8. The optimized nucleic acid sequence of VDBP1s is shown as SEQ ID No. 10 and the amino acid sequence corresponding thereto is shown as SEQ ID No. 11. The optimized nucleic acid sequence of VDBP2 is shown as SEQ ID No. 12, and the amino acid sequence corresponding thereto is shown as SEQ ID No. 13. The optimized nucleic acid sequence of VDBP1f tagged with a His-Tag is shown as SEQ ID No. 9; the optimized nucleic acid sequence of VDBP1s tagged with a His-Tag is shown as SEQ ID No. 14; and the optimized nucleic acid sequence of VDBP2 tagged with a His-Tag is shown as SEQ ID No. 15.

The VDBP expression vector of the present invention may further have a tag sequence such as a His-Tag, an HA-Tag and/or a FLAG-Tag for easily recovering VDBP from a culture medium of cells expressing the VDBP. For example, a Hs GcMAF-Gc1f-Histag sequence (SEQ ID No. 9) or a Hs GcMAF-Gc1s-Histag sequence (SEQ ID No. 14) formed by linking a His-Tag to a human GcMAF subtype Gc1f or Gc1s is preferable.

A VDBP expression vector is constructed by a method conventionally known to those skilled in the art and can be expressed in appropriate host cells, and thus the specific method is not particularly limited. The host cells into which a VDBP expression vector is to be transfected are not particularly limited as long as the cells can efficiently express VDBP. Examples of the host cells include CHO cells and HEK293 cells. Among them, CHO cells are preferable, and particularly, ExpiCHO™ (Gibco™) cells are preferable.

In the present invention, the cells transfected with a VDBP expression vector are cultured in a serum-free medium. The serum-free medium is not particularly limited as long as it is a medium containing no serum. Examples of the serum-free medium include an IMDM medium, a Medium 199, an Eagle's minimum essential medium (EMEM), an αMEM medium, a Dulbecco's modified Eagle's medium (DMEM), a Ham's F12 medium, an RPMI 1640 medium, a Fischer's medium, a MCDB201 medium, an ExpiCHO™ expression medium (Gibco™) and a mixed medium thereof. Among them, an ExpiCHO™ expression medium (Gibco™) is preferable.

To the serum-free mediums as mentioned above, if necessary, one or more serum substitutes, such as albumin, transferrin, fatty acid, insulin, sodium selenite, cholesterol, a collagen precursor, trace elements, 2-mercaptoethanol and 3'-thiol glycerol, may be added. To the mediums, if necessary, a substance, such as a lipid, amino acid, a protein, a 30 polysaccharide, a vitamin, a growth factor, a low molecular weight compound, an antibiotic substance, an antioxidant, pyruvic acid, a buffer and an inorganic salt, may further be added.

In the present invention, as a method for culturing cells transfected with a VDBP expression vector, it is preferable to employ a method of suspension-culturing the cells transfected with a VDBP expression vector in any one of the aforementioned serum-free mediums under the conditions of 37° C., 8% $CO_2$, and 120 rpm. The density of the cells to be cultured is $1\times10^3$ cells/mL to $1\times10^7$ cells/mL, preferably $1\times10^4$ cells/mL to $1\times10^6$ cells/mL and more preferably $1\times10^5$ cells/mL to $1\times10^6$ cells/mL. The number of culture days is 2 days to 14 days, preferably 3 days to 10 days and more preferably 5 days to 8 days. The number of culture days can be appropriately adjusted while monitoring the survival rate of the cells. When the cells transfected with a VDBP expression vector are cultured under such conditions, the active GcMAF having no sugar chain as a result of deglycosylation can be obtained in the culture medium, even though an enzymatic treatment is not carried out. Requiring no enzymatic treatment step for deglycosylation is one of the major characteristics of the method for producing active GcMAF of the present invention.

As a method for recovering active GcMAF from the culture medium obtained above, it is possible to employ a method using an affinity column, in which a resin allowing specific recovery of a protein having a tag such as the His-Tag is used. For example, in recovering a His-tagged protein, a metal chelate affinity column coordinated with a nickel ion can be utilized to recover the protein with high purity. After the protein is allowed to bind to the column, e.g., imidazole is added. In this manner, the His-Tag can dissociate from the nickel-coordinated column to elute active GcMAF having the His tag.

Examples of other methods for recovering active GcMAF from the culture medium obtained in the above include a method using a vitamin-D affinity column (also referred to as "Vit. D affinity column") such as a 25(OH)D3 Sepharose CL-6B column. More specifically, the culture medium obtained above is applied onto a HiPrep Sephacryl S300 column. The eluted sample is further applied onto a Vit. D affinity column (25(OH)D3 Sepharose CL-6B) to purify VDBP. A binding buffer containing 50 mM Tris-HCl, 15 mM EDTA, 150 mM NaCl and 0.1% TritonX100 (pH 7.4), and an elution buffer of a 6 M guanidine HCl can be used. The eluted sample is dialyzed against 10 mM Sodium phosphate, then subjected to SDS-PAGE, and stained with CBB to confirm that VDBP is purified as a single band. According to this method, VDBP can also be separated from a contaminant protein which is approximately 60 kDa.

The active GcMAF obtained by the method of the present invention has a function to activate macrophages. The function to activate macrophages herein refers to a function to facilitate the phagocytic capacity, particularly phagocytic capacity via an Fc receptor, active oxygen producing capacity, antigen presentation capacity and the like of macrophages. The active GcMAF obtained by the method of the present invention can be evaluated by treating mouse macrophages or the like with the active GcMAF and determining an improvement in phagocytic ability for SRBC (sheep red blood cells) via an Fc receptor. More specifically, the experimental method specifically described in the following Examples, Section 4, can be used.

EXAMPLES

The present invention will be more specifically described by way of the following Examples; however, the present invention is not limited by these Examples.

1. One-Step Method for Synthesizing Active GcMAF by Using CHO Cells/Serum-Free Medium/Suspension Culture System ExpiCHO™ (Gibco™) cells were transfected with a human VDBP1f expression vector (obtained by inserting a Hs GcMAF-Gc1f-Histag into a site downstream of the CMV promoter of pcDNA3.4-TOPO (Thermo Fisher Scientific); hereinafter, referred to as Hs GcMAF-Gc1f-Histag vector) and a GALANT3 gene expression vector (16ACJOMP_GALNT3_pcDNA3.4-TOPO; invitrogen), and the cells were suspension-cultured in a serum-free medium (ExpiCHO™ expression medium, Gibco™). Culture was carried out in accordance with the Protocol of Gibco™ ExpiCHO™ expression system. The amounts (μg) of Hs GcMAF-Gc1f-Histag vector and GALANT3 gene expression vector and the Culture volume (mL) were as shown in the following Table 1.

TABLE 1

| | Hs GcMAF-Gc1F-Histag (μg) | GALANT3 (μg) | Culture volume (mL) |
| --- | --- | --- | --- |
| Condition 1 | 15 | 2 | 30 |
| Condition 2 | 20 | 2 | 25 |

Figure 2:
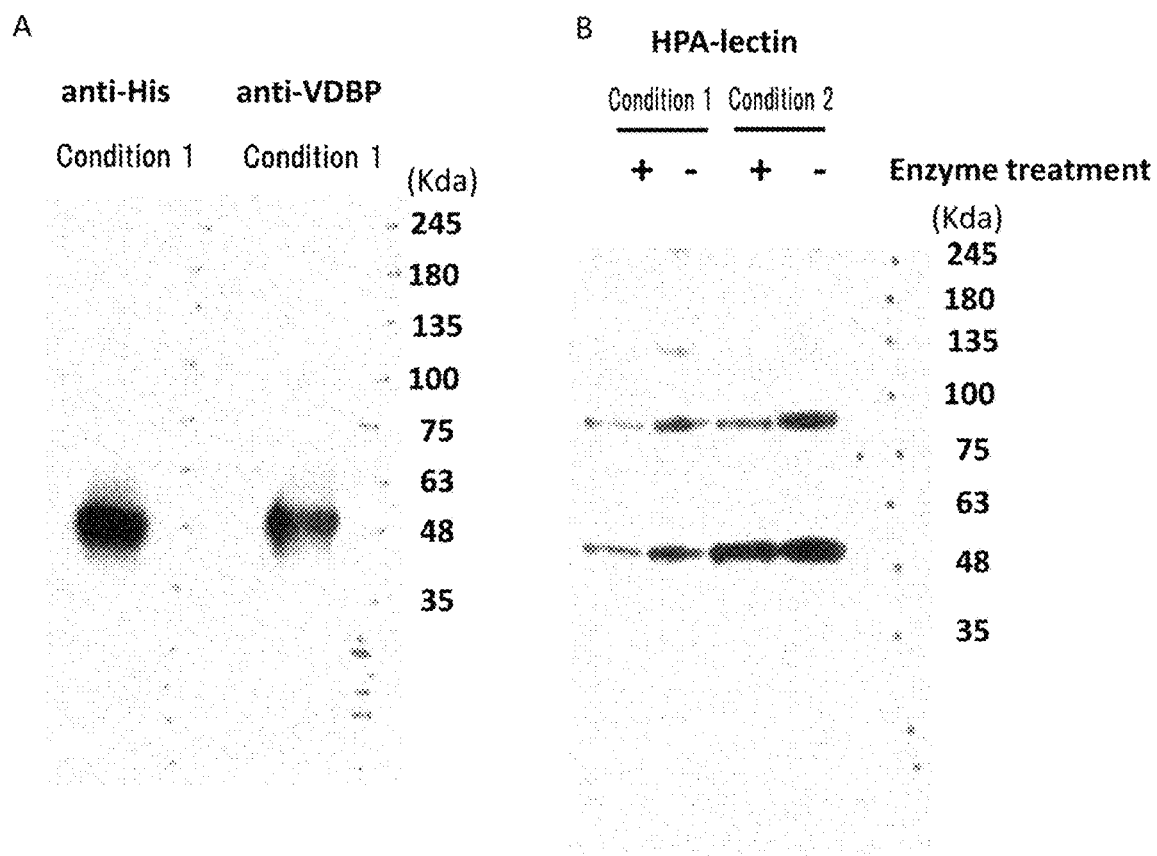
FIG. 2 shows the results of Western Blotting of active GcMAF obtained by using the method of the present invention (CHO cells/serum-free medium/suspension culture system).

After culturing for 8 days, the cell-culture supernatant was applied onto a His-Trap column (manufactured by GE healthcare). The trapped proteins were collected and dialyzed against a 50 mM sodium phosphate buffer (pH 7.0). After the dialysis, the sample was separated by SDS-PAGE, and the proteins were transferred onto a membrane. Western Blot was carried out by using an anti-His antibody or an anti-DVBP antibody (FIG. 2A). Further, VDBPs (5 μg) obtained from the "condition 1" and "condition 2" were treated with 1 mU sialidase (Neuraminidase) and 1 mU galactosidase (β-D-Galactosidase) at 37° C. for 3 hours. The samples treated with the enzymes and the samples not treated with the enzymes were separately subjected to SDS-PAGE and analyzed for sugar chain structure by blotting with a lectin (biotin conjugated HPA lectin) capable of reacting with GalNAc. As a result, the samples not treated with the enzymes were also reactive to HPA lectin. It was thus demonstrated that active GcMAF can be obtained by use of the serum-free medium/suspension culture system of the present invention even if the above enzymatic treatment is not carried out. The amount of VDBP reacted with HPA lectin did not increase even when the enzymatic treatment was carried out. It was thus demonstrated that almost the whole amount of VDBP can be obtained as active GcMAF by use of the serum-free medium/suspension culture system of the present invention is used (FIG. 2B).

Figure 3:
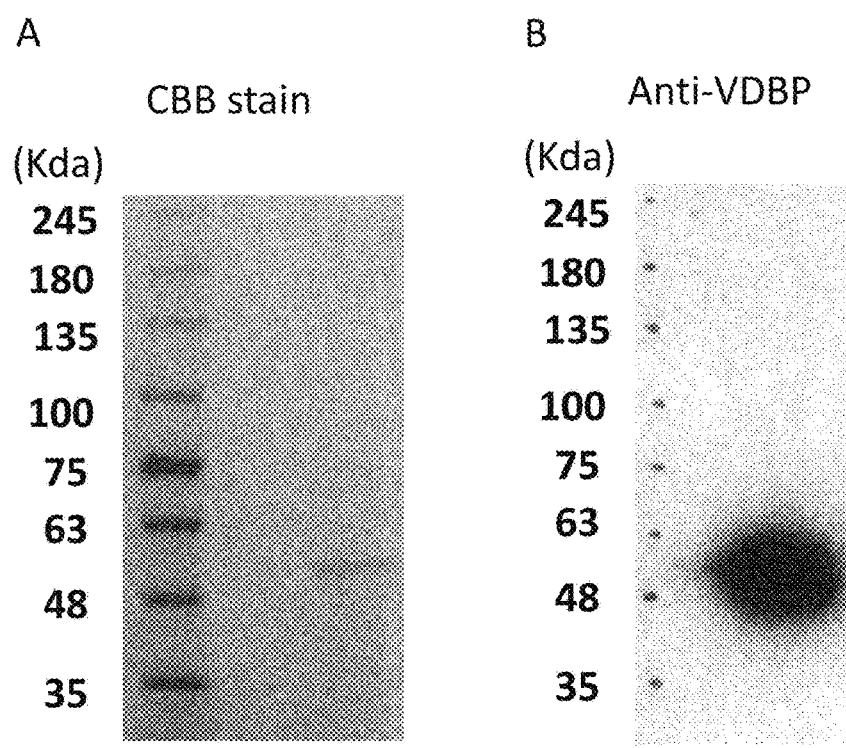
FIG. 3 shows the results of SDS-PAGE (CBB stain) and Western Blotting of active GcMAF (after purifying by vitamin-D affinity column) obtained by using the method of the present invention (CHO cells/serum-free medium/suspension culture system).

The above mentioned VDBP samples were each separated by SDS-PAGE and stained with CBB. As a result, an apparent VDBP band at near 53 kDa and another band at near 60 kDa were observed. To separate the VDBP band at near 53 kDa and the band at near 60 kDa, the sample was applied onto a HiPrep Sephacryl S300 column followed by applying the eluted sample onto a Vit. D affinity column (25(OH)D3 sepharose CL-6B) to purify the VDBP. As a binding buffer, a solution containing 50 mM Tris-HCl, 15 mM EDTA, 150 mM NaCl and 0.1% Triton® X-100 (pH 7.4) was used. As an elution buffer, 6 M guanidine HCl was used. The eluted sample was dialyzed against 10 mM sodium phosphate, then subjected to SDS-PAGE and stained with CBB. It was demonstrated that the VDBP is purified as a single band by purification with a Vit. D affinity column; more specifically, can be separated from a band at near 60 kDa (FIG. 3A). Further, the single band was recognized by an anti-VDBP antibody in western blotting (FIG. 3B).

As mentioned above, it was found that active GcMAF can be produced in one step by a production method of VDBP using the CHO cells/serum-free medium/suspension culture system, but at the same time, a contaminant protein which is approximately 60 kDa is present. It was confirmed that GcMAF and the 60 kDa contaminant protein can be separated for purification by means of a Vit. D affinity column.

The results demonstrate that when VDBP is produces by using the CHO cells/serum-free medium/suspension culture system of the present invention, the active GcMAF to which only GalNAc linked can be produced in one step. Furthermore, a contaminant protein which is approximately 60 kDa can be efficiently separated off by use of a Vit. D affinity column. According to the method of the present invention, the GcMAF is highly expressed (3 to 5 mg/20 mL culture). In this sense, the method of the present invention may be as the most suitable one-step production method for active GcMAF, as far as known at present.

2. Study of Expression Induction of GALANT3 Affecting GcMAF Production

Whether the linking efficiency of GalNAc to the 418/420th threonine of VDBP is influenced by co-expression of a glycosylation enzyme such as GALANT3 was analyzed.

ExpiCHO™ (Gibco™) cells were transfected with a human VDBP1f expression vector and a GALANT3 gene expression vector, and the cells were suspension-cultured in a serum-free medium (ExpiCHO™ expression medium, Gibco™). Culture was carried out in accordance with the Protocol of Gibco™ ExpiCHO™ expression system. The amounts (μg) of Hs GcMAF-Gc1f-Histag vector and GALANT3 gene expression vector and the Culture volume (mL) were as shown in the following Table 2.

TABLE 2

|  | Hs GcMAF-Gc1F-Histag (μg) | GALANT3 (μg) | Culture volume (mL) |
|---|---|---|---|
| Condition 1 | 20 | 10 | 25 |
| Condition 2 | 20 | 4 | 25 |
| Condition 3 | 20 | 0 | 25 |

Figure 4:
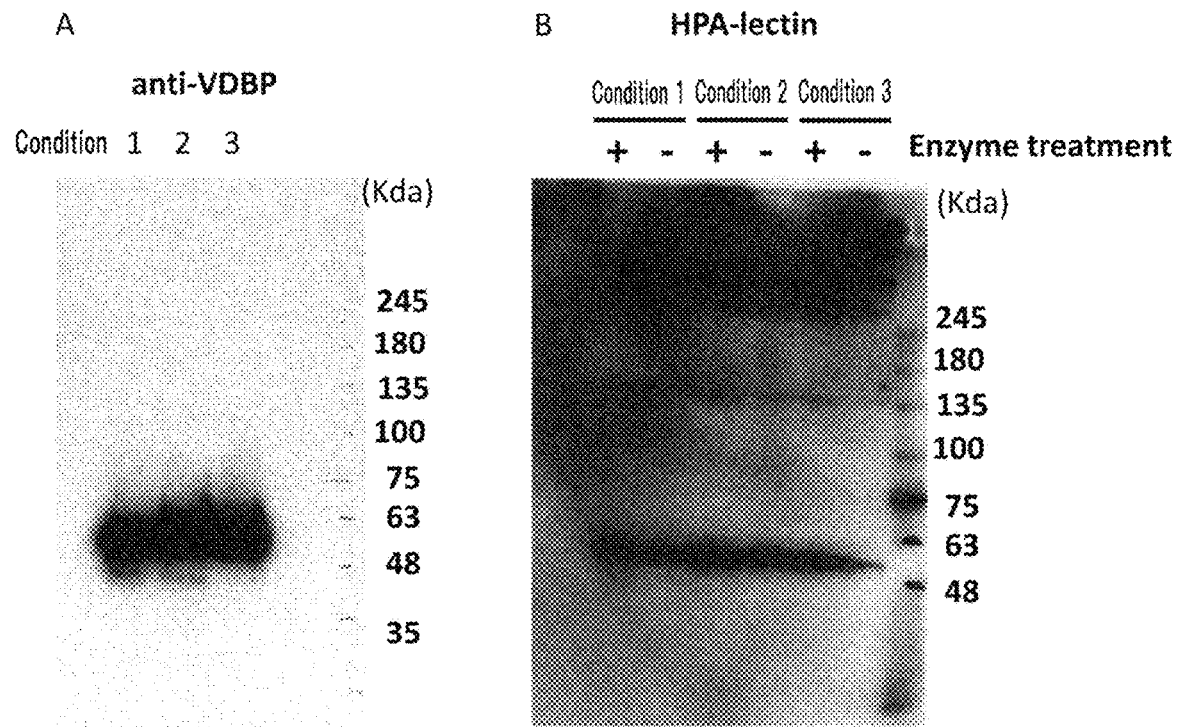
FIG. 4 shows the examination results on an effect of expression of GALANT3 (N-acetyl galactosaminyl transferase 3) on production of active GcMAF.

After culturing for 7 days (37° C., 8% $CO_2$, 120 rpm), the cell-culture supernatant was applied onto a His-Trap column (GE healthcare). The trapped proteins were collected and dialyzed against a 50 mM sodium phosphate buffer (pH 7.0). The eluted sample was separated by SDS-PAGE, and the proteins were transferred onto a membrane. Western Blot was carried out by using an anti-VDBP antibody (FIG. 4A). Further, the sugar chain structure was analyzed with biotin conjugated HPA lectin which is capable of reacting with GalNAc (FIG. 4B). Even under the conditions using no GALANT3 (condition 3), the band was reactive to HPA lectin. It was therefore demonstrated that co-expression of GALANT3 does not influence the expression level of the VDBP and GalNAc glycosylation efficiency.

The result shows that co-expression of a glycosylation enzyme GALANT3 does not influence the expression level of VDBP and GalNAc glycosylation efficiency. The possibility that the glycosylation enzyme has been originally expressed in a sufficient level in CHO cells was considered. More specifically, also in a one-step method for producing active GcMAF by using the CHO cells/serum-free medium/suspension culture system of the present invention, co-expression of GALANT3 is certainly not essential in ExpiCHO™ (Gibco™) cells.

3. Measurement of Phagocytic Activity of Macrophages Through Active GcMAF Produced by One-Step Method of the Present Invention ICR mice (female) of 7 weeks old were purchased from Japan SLC, Inc. After cervical dislocation, the skin was stripped off. Into the abdominal cavity of the ICR mice, cold DPBS (5 ml) was injected. The abdomen was rubbed, and then, the peritoneal fluid containing peritoneal cells was collected and centrifuged 1,000 rpm for 15 minutes at 4° C. The supernatant was removed, and then an appropriate amount of RPMI1640 medium (THERMOFICHER SCIENTIFIC) was added. The cells were stained with trypan blue and counted. The density of the cells was adjusted by RPMI1640 medium to $1.0 \times 10^6$ cells/mL and 500 μL of the resultant cell suspension was inoculated to each well of a plate, in which a cover glass was previously sunk, to $5.0 \times 10^5$ cells/well. RPMI1640 medium (500 μL) was further added and pre-culture was carried out at 37.5° C. for one hour to allow macrophages to attach onto the cover glass. The supernatant was removed and the layer of attached macrophages was washed. RPMI1640 medium was added and culture was carried out at 37° C., overnight. The supernatant was removed and 990 μL of RPMI1640 medium was added. The active GcMAF (1 ng) (10 μL, final concentration 1 ng/mL) obtained by purifying in the above was added. As a positive control, 1 μg of a lipopolysaccharide (LPS, Sigma) (10 μL, final concentration 1 μg/mL) was added. Culture was carried out under the conditions of 37° C. and 5% $CO_2$ for 3 hours. After removal of the supernatant, 0.5% SRBC (CEDARLANE, CLD68) opsonized with IgG by reaction with Anti-Sheep Red Blood Cell Stroma antibody (Abcam plc., ab50674) was added and allowed macrophages to ingest the SRBCs for 90 minutes. The cover glasses were taken out from the wells and dried at room temperature. Macrophages were fixed with methanol, dried by a dryer, and stained by using a Giemsa staining solution diluted 20 fold with DPBS for one hour. The cover glasses were washed with tap water and dried at room temperature overnight. The cover glasses were allowed to adhere to glass slides and observed by a microscope (400 magnification). The ingested SRBCs were counted and the ingestion index was calculated by the following formula to evaluate the phagocytic activity of the macrophages. The results are shown in FIG. 5.

$$\frac{\text{Phagocytosis } m\Phi}{\text{Total } m\Phi} \times \frac{\text{Number of ingested } SRBCs}{\text{Phagocytosis } m\Phi} = \text{ingestion index} \quad \text{[Numerical Formula 1]}$$

Figure 5:
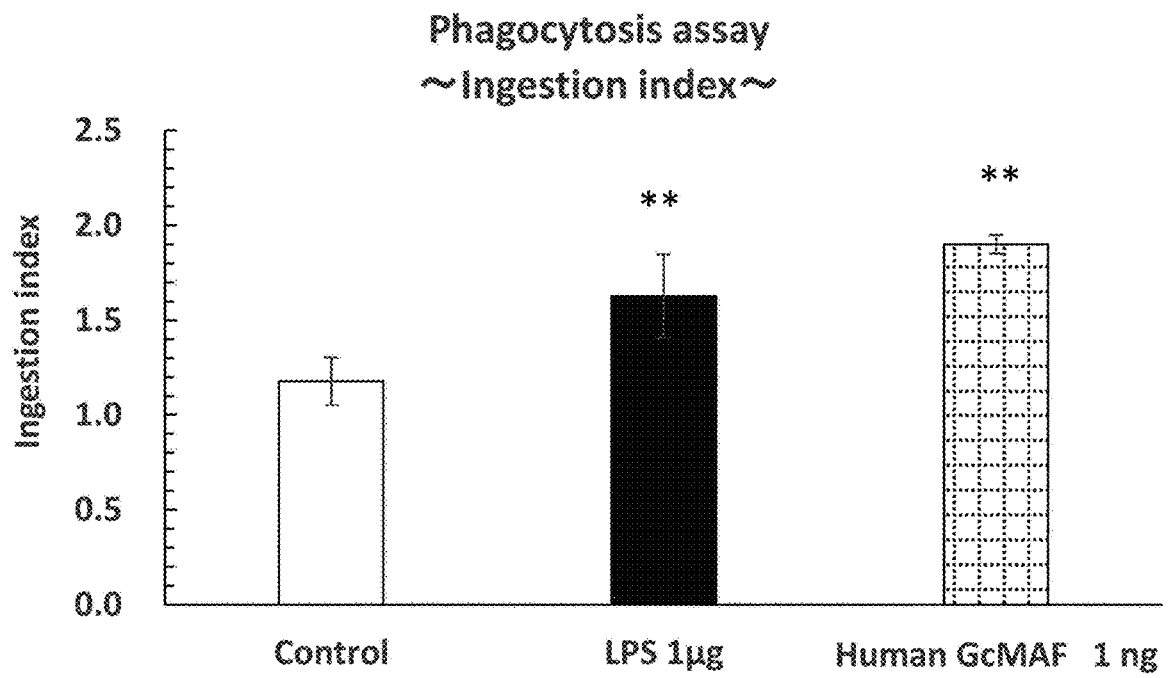
FIG. 5 shows the macrophage activation ability of active GcMAF obtained by using the method of the present invention (CHO cells/serum-free medium/suspension culture system).

As shown in FIG. 5, it was found that the GcMAF obtained by the CHO cells/serum-free medium/suspension culture system of the present invention has an effect to facilitate the phagocytic capacity of macrophages (macrophage activation effect). The GcMAF obtained by the CHO cells/serum-free medium/suspension culture system of the present invention exhibited a macrophage activation effect corresponding to that of 1 μg/mL of LPS used as a positive control in a dose as low as 1 ng/mL. Consequently, according to the method of the present invention, active GcMAF having a high specific activity can be obtained efficiently.

4. One-Step Method for Producing Active GcMAF Subtypes (1f, 1s, 2) Using CHO Cells/Serum-Free Medium/Suspension Culture System ExpiCHO™ (Gibco™) cells were transfected with a human VDBP1f, VDBP1s or VDBP2 expression vector, and the cells were suspension-cultured in a serum-free medium (ExpiCHO™ expression medium, Gibco™). Culture was carried out in accordance with the Protocol of Gibco™ ExpiCHO™ expression system. Hs GcMAF-Gc1s or Hs GcMAF-Gc2-Histag was used in an amount of 15 μg.

Figure 6:
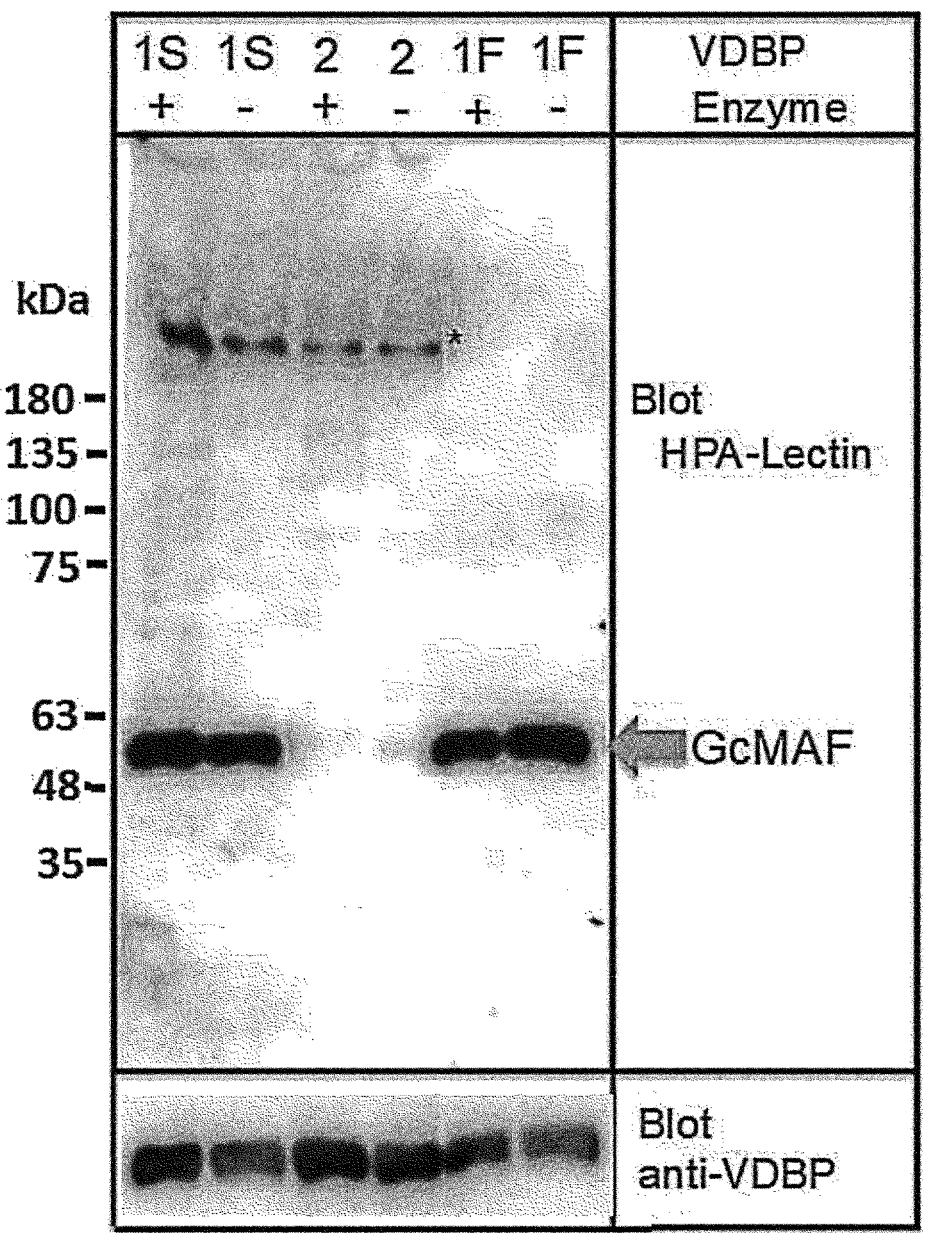
FIG. 6 shows the results of Western Blotting of active GcMAF obtained by using the method of the present invention (CHO cells/serum-free medium/suspension culture system).

After culturing for 8 days, the cell-culture supernatant was applied onto a His-Trap column (manufactured by GE healthcare). The trapped proteins were collected and dialyzed against a 50 mM sodium phosphate buffer (pH 7.0). After the dialysis, the sample was separated by SDS-PAGE. VDBP (5 μg) was treated with 1 mU sialidase (neuraminidase) and 1 mU galactosidase (β-D-galactosidase) at 37° C. for 3 hours. The samples treated with the enzymes and the samples not treated with the enzymes were separately subjected to SDS-PAGE and analyzed sugar chain structure by blotting with a lectin (biotin conjugated HPA lectin) capable of reacting with an anti-VDBP antibody and GalNAc. Note that 1f subtype was produced by the method described in the section "1. One-step method for producing active GcMAF by using CHO cells/serum-free medium/suspension culture system", treated with a Vit. D affinity column (25(OH)D3 sepharose CL-6B) and used as a sample. As a result, the samples of 1s and 1f subtypes not treated with the enzymes were also reactive to HPA lectin. It was thus demonstrated that active GcMAF can be obtained by use of the serum-free medium/suspension culture system of the present invention even if the above enzymatic treatment is not applied. The amount of VDBP reacted with HPA lectin did not increase even when the enzymatic treatment was applied. It was thus demonstrated that almost the whole amount of VDBP can be obtained as active GcMAF by use of the serum-free medium/suspension culture system of the present invention (FIG. 6).

Figure 8:
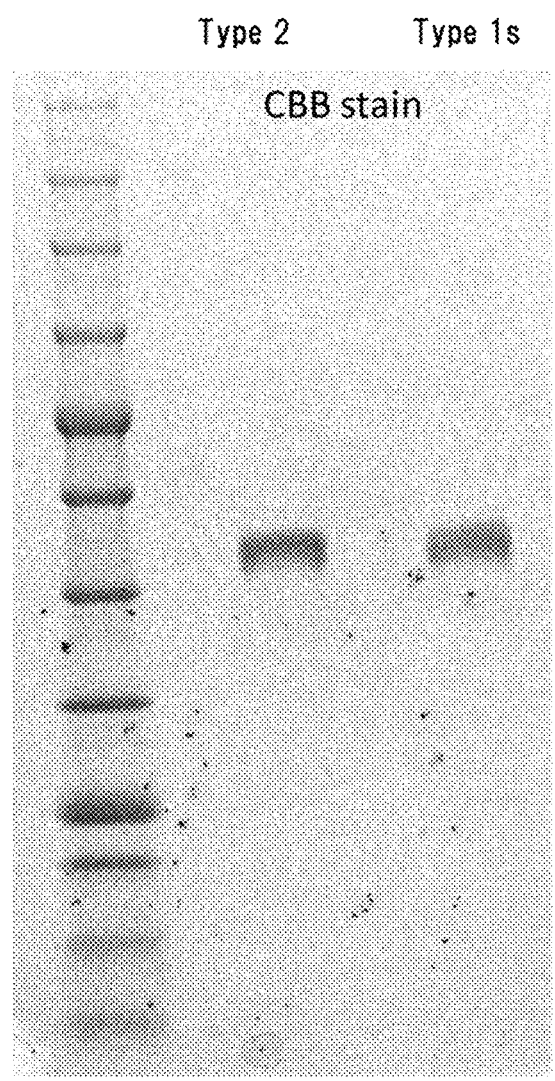
FIG. 8 shows the results of SDS-PAGE (CBB stain) of active GcMAF (after purifying by vitamin-D affinity column) obtained by using the method of the present invention (CHO cells/serum-free medium/suspension culture system).

After the dialysis, VDBP samples were applied onto a HiPrep Sephacryl S300 column. The eluted samples were applied onto a Vit. D affinity column (25(OH)D3 sepharose CL-6B) to purify VDBP. As a binding buffer, a solution containing 50 mM Tris-HCl, 15 mM EDTA, 150 mM NaCl and 0.1% Triton® X-100 (pH 7.4) was used. As an elution buffer, 6 M guanidine HCl was used. The eluted samples were dialyzed against 10 mM sodium phosphate, then subjected to SDS-PAGE and stained with CBB. It was demonstrated that VDBP is purified as a single band by purification with the Vit. D affinity column; more specifically, can be separated from a band at near 60 kDa (FIG. 8).

5. One-Step Method for Producing Active GcMAF by Using HEK293/Serum-Free Medium/Suspension Culture System Expi 293 (Gibco™) cells were transfected with a human VDBP1f expression vector, and the cells were suspension-cultured in a serum-free medium (ExpiCHO™ expression medium, Gibco™). Culture was carried out in accordance with the Protocol of Gibco™ Expi293 expression system. The VDBP1f expression vector (Hs GcMAF-Gc1f-Histag vector) was used in an amount of 20 μg.

Figure 7:
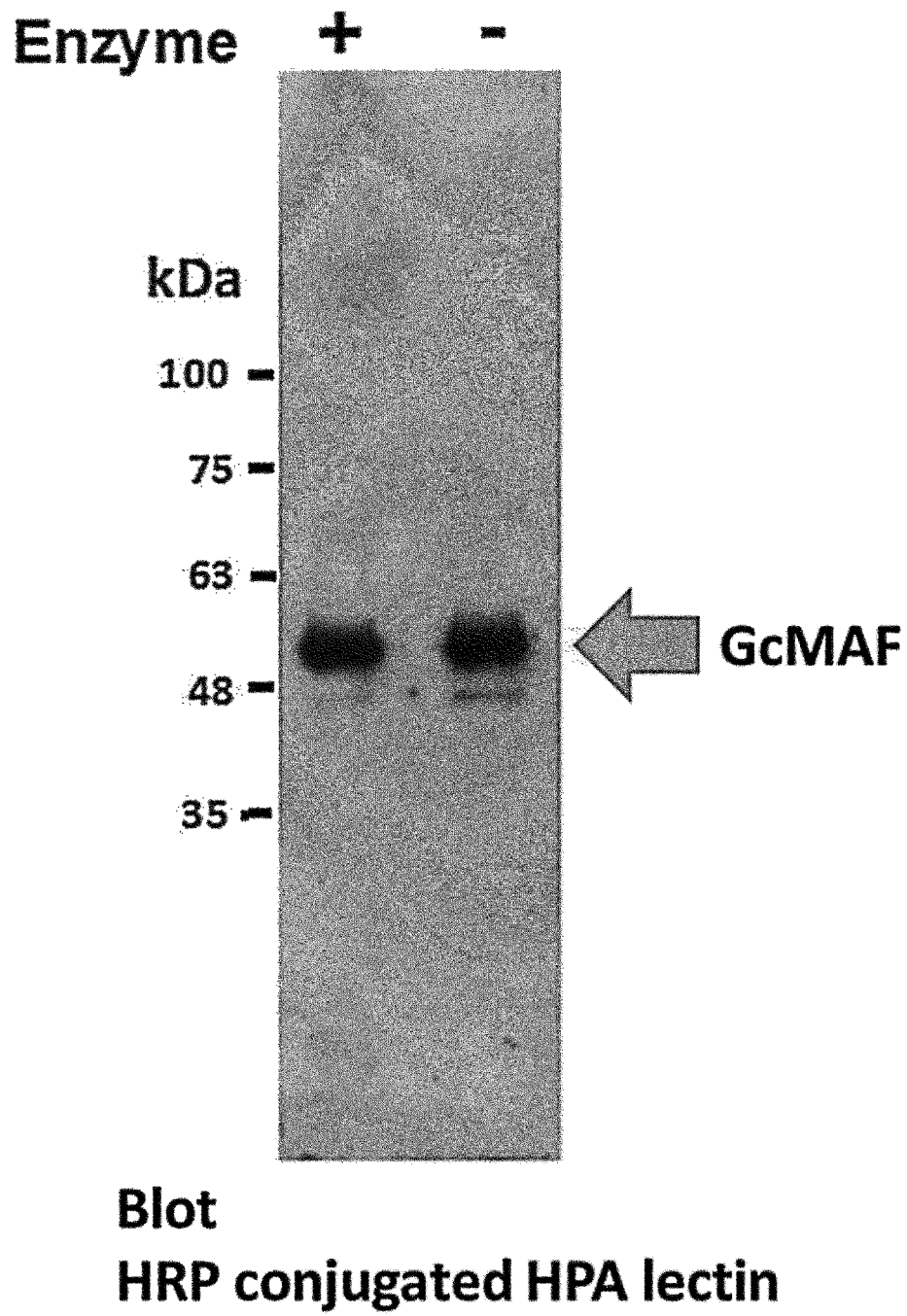
FIG. 7 shows the results of Western Blotting of active GcMAF obtained by using the method of the present invention (HEK293 cells/serum-free medium/suspension culture system).

After culturing for 8 days, the cell-culture supernatant was applied onto a His-Trap column (GE healthcare). The trapped proteins were collected and dialyzed against a 50 mM sodium phosphate buffer (pH 7.0). VDBP (5 μg) was treated with 1 mU sialidase (neuraminidase) and 1 mU galactosidase (β-D-galactosidase) at 37° C. for 3 hours. The samples treated with the enzymes and the samples not treated with the enzymes were separately subjected to SDS-PAGE and analyzed sugar chain structure by blotting with a lectin (biotin conjugated HPA lectin), which reacts with GalNAc. As a result, the samples not treated with enzymes were also reactive to HPA lectin. It was thus demonstrated that when the HEK293 cells are used as host cells, active GcMAF can be obtained even if the above enzymatic treatment is not applied, similarly to the case of CHO cells (FIG. 7).

As described in the foregoing, according to the method for producing active GcMAF by using the host cells/serum-free medium/suspension culture system of the present invention, it was found that active GcMAF can be efficiently produced by one step without an enzymatic treatment step for deglycosylation.

INDUSTRIAL APPLICABILITY

According to the method for producing active GcMAF of the present invention employing a step of expressing VDBP by cultured cells, it is not necessary to collect serum, plasma or the like and is also easy to mass-produce the active GcMAF. In addition, it is not necessary to carry out a step of purifying VDBP from serum, plasma or the like, and an enzymatic treatment step for deglycosylation. Therefore, the active GcMAF can be efficiently and conveniently produced by fewer steps. Since the active GcMAF, which has been hardly produced in a large quantity, can be easily mass-produced by the present invention, the active GcMAF can be suitably used in medicines and healthy foods as an active ingredient.

The invention claimed is:

1. A method for producing active Gc protein-derived macrophage activating factor (GcMAF), comprising suspension culturing Chinese hamster ovary (CHO) cells that have been transfected with a vitamin-D binding protein expression vector in a serum-free medium, wherein the method does not comprise an enzymatic treatment step for deglycosylation, wherein the vitamin-D binding protein expression vector is one in which a nucleic acid encoding VDBP1f or VDBP1s is inserted, and wherein expression of the vitamin-D binding protein expression vector by the suspended CHO cells in the serum-free medium produces the active GcMAF.

2. The method for producing active GcMAF according to claim 1, comprising a purification step by a vitamin-D affinity column.

3. The method for producing active GcMAF according to claim 1, wherein the active GcMAF is expressed in an amount of 3 to 5 mg per 20 mL culture.

4. The method for producing active GcMAF according to claim 1, wherein the nucleic acid comprises a sequence selected from the group consisting of SEQ ID No. 1 and SEQ ID No. 2.

5. The method for producing active GcMAF according to claim 1, wherein the nucleic acid encodes an amino acid sequence selected from the group consisting of SEQ ID No. 4 and SEQ ID No. 5.

* * * * *